(12) United States Patent
Wehba et al.

(10) Patent No.: US 8,768,719 B2
(45) Date of Patent: Jul. 1, 2014

(54) MEDICATION ADMINISTRATION AND MANAGEMENT SYSTEM AND METHOD

(75) Inventors: Steven R. Wehba, Carlsbad, CA (US); Jeffrey Eugene Rinda, San Diego, CA (US); Barbara Mary Trohimovich, San Diego, CA (US); Jeff Pelletier, Fox River Grove, IL (US)

(73) Assignee: Hospira, Inc., Lake Forest, IL (US)

( * ) Notice: Subject to any disclaimer, the term of this patent is extended or adjusted under 35 U.S.C. 154(b) by 943 days.

(21) Appl. No.: 11/692,781

(22) Filed: Mar. 28, 2007

(65) Prior Publication Data
US 2007/0233521 A1    Oct. 4, 2007

Related U.S. Application Data

(60) Provisional application No. 60/786,599, filed on Mar. 28, 2006.

(51) Int. Cl.
| | |
|---|---|
| *G06Q 50/00* | (2012.01) |
| *G06F 19/00* | (2011.01) |
| *A61M 5/142* | (2006.01) |
| *G06Q 50/24* | (2012.01) |
| *G06Q 50/22* | (2012.01) |

(52) U.S. Cl.
CPC ....... *A61M 5/142* (2013.01); *A61M 2205/6018* (2013.01); *G06F 19/3412* (2013.01); *G06Q 50/24* (2013.01); *A61M 2205/6072* (2013.01); *G06Q 50/22* (2013.01); *A61M 2205/50* (2013.01); *G06F 19/3468* (2013.01)
USPC .................................. 705/2; 705/3; 600/300

(58) Field of Classification Search
CPC .... G06Q 50/22; G06Q 50/24; G06F 19/3456; G06F 19/322; G06F 19/3406; G06F 19/3481; G06F 19/326; G06F 19/327; G06F 19/3468; G06F 19/30; G06F 19/34
USPC ............................................ 705/2–3; 600/300
See application file for complete search history.

(56) References Cited

U.S. PATENT DOCUMENTS

| | | |
|---|---|---|
| 4,835,372 A | 5/1989 | Gombrich et al. |
| 4,857,716 A | 8/1989 | Gombrich et al. |
| 5,317,506 A | 5/1994 | Coutre et al. |
| 5,594,786 A | 1/1997 | Chaco et al. |
| 5,713,856 A | 2/1998 | Eggers et al. |
| 5,781,442 A | 7/1998 | Engelson et al. |
| 5,814,015 A | 9/1998 | Gargano et al. |
| 5,822,544 A | 10/1998 | Chaco et al. |
| 5,990,838 A | 11/1999 | Burns et al. |
| 6,135,949 A | 10/2000 | Russo et al. |
| 6,346,886 B1 | 2/2002 | De La Huerga |
| 6,408,330 B1 | 6/2002 | De La Huerga |
| 6,519,569 B1 | 2/2003 | White et al. |
| 6,542,902 B2 | 4/2003 | Dulong et al. |
| 6,544,228 B1 | 4/2003 | Heitmeier |

(Continued)

*Primary Examiner* — Sind Phongsvirajati
(74) *Attorney, Agent, or Firm* — Michael R. Crabb

(57) ABSTRACT

A system, method and computer program for programming a medical device to administer a medication to a patient includes the medical device, a scanner that may be associated with a point of care (POC) system, and a medication management unit (MMU). A computer in the POC system can directly program the medical device with the permission of the MMU after a full "five rights" check or the "right patient" check can be delayed until after the pump program is downloaded. Other workflows are disclosed for programming the medical device in manual, semi-automatic and automatic modes, with safety checks incorporated at various points.

7 Claims, 21 Drawing Sheets

(56) References Cited

U.S. PATENT DOCUMENTS

| | | |
|---|---|---|
| 6,571,294 B2 | 5/2003 | Simmon et al. |
| 6,647,299 B2 | 11/2003 | Bourget |
| 6,671,563 B1 | 12/2003 | Engleson et al. |
| 6,790,198 B1 | 9/2004 | White et al. |
| 6,985,870 B2 | 1/2006 | Martucci et al. |
| 7,117,041 B2 * | 10/2006 | Engleson et al. ............. 700/2 |
| 7,154,397 B2 | 12/2006 | Zerhusen et al. |
| 7,224,979 B2 | 5/2007 | Singhal et al. |
| 7,289,815 B2 | 10/2007 | Gfeller et al. |
| 7,471,994 B2 | 12/2008 | Ford et al. |
| 2001/0044731 A1 * | 11/2001 | Coffman et al. ............. 705/3 |
| 2001/0056358 A1 | 12/2001 | Dulong et al. |
| 2002/0038392 A1 | 3/2002 | De La Huerga |
| 2003/0140928 A1 | 7/2003 | Bui et al. |
| 2003/0236683 A1 | 12/2003 | Henderson et al. |
| 2004/0019607 A1 | 1/2004 | Moubayed et al. |
| 2004/0064435 A1 | 4/2004 | Moubayed et al. |
| 2004/0128162 A1 | 7/2004 | Schlotterbeck et al. |
| 2004/0167804 A1 * | 8/2004 | Simpson et al. ............. 705/3 |
| 2004/0172222 A1 * | 9/2004 | Simpson et al. ............. 702/189 |
| 2004/0176984 A1 | 9/2004 | White et al. |
| 2004/0193328 A1 | 9/2004 | Zaitsu et al. |
| 2004/0193453 A1 | 9/2004 | Butterfield et al. |
| 2005/0055242 A1 * | 3/2005 | Bello et al. ............. 705/2 |
| 2005/0055244 A1 * | 3/2005 | Mullan et al. ............. 705/2 |
| 2005/0065817 A1 * | 3/2005 | Mihai et al. ............. 705/2 |
| 2005/0086071 A1 | 4/2005 | Fox, Jr. et al. |
| 2005/0086072 A1 | 4/2005 | Fox et al. |
| 2005/0119914 A1 | 6/2005 | Batch |
| 2005/0144043 A1 | 6/2005 | Holland et al. |
| 2005/0251418 A1 | 11/2005 | Fox, Jr. et al. |
| 2005/0277873 A1 | 12/2005 | Stewart et al. |
| 2005/0277890 A1 | 12/2005 | Stewart et al. |
| 2005/0278194 A1 | 12/2005 | Holland et al. |
| 2006/0026205 A1 | 2/2006 | Butterfield |
| 2006/0047538 A1 | 3/2006 | Condurso et al. |
| 2006/0053036 A1 | 3/2006 | Coffman et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106449 A1 | 5/2006 | Ben Muvhar |
| 2006/0106649 A1 * | 5/2006 | Eggers et al. ............. 705/3 |
| 2006/0190302 A1 | 8/2006 | Eggers et al. |
| 2006/0229551 A1 | 10/2006 | Martinez et al. |
| 2007/0214003 A1 | 9/2007 | Holland et al. |

* cited by examiner

:PDAAPP01_2004

File    Zoom    Tools    Help

Caregiver Task List

Name: Holland, Neil

NS 1000 mL

|  | Ordered | Pump |
|---|---|---|
| Perform Date | 02-20-2004 ▼ | |
| Perform Time | 4:45:00 PM ▲▼ | |
| Bag # | – | |
| Volume (mL) | 1000 | 1000.00 |
| Rate (mL / hr) | 10 | 10.00 |
| Site | ▼ | |
| Backpress | – | 1.00 |

Pump Running

[Cancel]                                [Complete]

FIG. 6

MEDICATION ADMINISTRATION AND MANAGEMENT SYSTEM AND METHOD

CROSS-REFERENCE TO RELATED APPLICATIONS

This application claims the priority of U.S. Provisional Patent Application No. 60/786,599, filed Mar. 28, 2006, which is incorporated by reference herein in its entirety.

BACKGROUND OF THE INVENTION

The present invention relates to the field of delivering medication to patients, more particularly to an integrated system for maximizing patient safety and caregiver productivity for medication delivery.

Modern medical care often involves the use of medical pump devices to deliver fluids and/or fluid medicine to patients. Medical pumps permit the controlled delivery of fluids to a patient, and such pumps have largely replaced gravity flow systems, primarily due to the pump's much greater accuracy in delivery rates and dosages, and due to the possibility for flexible yet controlled delivery schedules. However, modern medical devices, including medical pumps, can be complicated and time-consuming for caregivers to program. Medical facilities struggle to provide appropriate caregiver staffing levels and training while holding down the cost of medical care. Human errors in pump programming and other medication errors can have adverse or even deadly consequences for the patient. Medication errors, which are sometimes referred to as adverse drug events (ADE), can increase the length of hospital stay and the cost of medical care for the patients involved or their healthcare insurance carrier.

Therefore, a principal objective of this invention is to provide an integrated medication management system that is flexible, reduces the risks of medication error, improves patient safety, and improves caregiver productivity.

These and other objectives will be apparent to those skilled in the art.

A SUMMARY OF THE INVENTION

A system, method and computer program product for administering a medication to a patient with a medical device includes a point of care (POC) system and a medication management unit (MMU) in communication with each other. A computer in the POC system can directly program the medical device with the assistance or permission of the MMU after a full "five rights" check using an input device for receiving identification information. A full five rights check ensures that the right medication in the right dose or rate through the right device channel or route at the right time is administered to the right patient. Alternatively, a "right patient" check can be delayed until after the pump program has been downloaded to the pump by the POC system or the MMU.

The present invention is directed to a medication management system which includes various computers, including a medication management unit (MMU) associated with a medical device for performing a medication order. The medication management system is flexible and integrated to provide for enhanced patient safety and caregiver productivity with a variety of hospital information and point of care systems. The medication management system can take various forms and provides methods for administering the right medication in the right dose or rate through the right device channel or route at the right time to the right patient. By confirming the accuracy of the drug, dose, patient, time, and route, medication errors at the bedside can be prevented before an ADE occurs. The caregiver confirms and starts the infusion of the medication order at the pump only if these bits of identification information match the order.

The MMU is able to determine the network IP address of a medical device it is in wireless communication with based on the factory-established or hospital-established logical address of the medical device. The MMU monitors the general physical location of a medical device based on the last access node used by the wireless connectivity capability in the medical device.

The device is capable of storing two, simultaneous versions of a drug library—one in primary memory and another in cache memory. Upon occurrence of a triggering event, the device will receive an updated drug library, store it in its cache, and ultimately replace the existing drug library in primary memory with the new library in the cache. During execution of a medication order, the medical device utilizes the drug library in its primary memory.

In other embodiments of the medication management system of this invention, the MMU receives medication order and delivery information from an information system directly through an electronic network or indirectly through a wireless handheld point of care (POC) input (scanning) device, such as a personal digital assistant (PDA). The PDA transmits the delivery information and the medication order in the form of an infusion delivery order that may include various pieces of information including but not limited to an infusion rate to the MMU.

The MMU translates the simple infusion rate of the delivery order into delivery programming code or information suitable for automatically programming the designated pump and further checks the delivery order and delivery programming code against a variety of drug library parameters (including but not limited to hard and/or soft limits for drug delivery rates, dose, volume, duration, route and site of administration), patient-specific safety factors, and clinical decision support rules including drug compatibility and drug-drug interactions. The MMU can be configured by the user at the MMU console or client workstation to monitor the status of the pump and the infusion (including alarms, event logs, and pump user interface inputs), generate reports, and control the distribution of drug library and operating software code updates to one or more pumps. A drug library editor (DLE) deployed as a part of the MMU, its console, or on a separate computer (DLE client workstation), enables the user to import, export and edit whole drug libraries and individual drug library values to control and customize a drug library according to hospital preferences.

The MMU and/or the POC system saves the caregiver time by automatically populating or programming data entry fields in the pump that previously had to be entered manually. The medication management system of this invention enhances patient safety by minimizing manual entries. The system also enhances patient safety by screening drug delivery orders for conformance with established hospital practices, expert or clinical decision support rules and recommendations before, or more preferably immediately before, the pump begins to execute the order. The caregiver is provided with a least one and preferably several opportunities to catch a medication error before it happens. The caregiver can confirm the order at the point of care (POC) system and/or before starting the infusion at the pump. The system is flexible enough to permit human interventions and overrides, and tracks such events for documentation, reporting, benchmarking and trouble-shooting purposes.

In one embodiment, a method is provided for administering a medication to a patient with a medical device. The medical device can be an infusion pump, and the medication can be a medication solution for infusion into the patient. The method receives at a first computer, in communication with a second computer, caregiver specific identification information, drug container specific identification information, medical device specific identification information, with one or more identification receivers or input devices, such as a hand-held wireless personal digital assistant (PDA) having barcode scanner for scanning barcoded information. The drug container specific identification information is located on a container containing the medication. The first computer can be computer in a POC system and the second computer can be a medication management computer, such as the MMU mentioned above and further described below. The caregiver specific identification information can include the identification of a specific caregiver (i.e., name, social security number, ID number, and/or some other identifier), or provide "look-up" information for retrieving the identification of a specific caregiver. The medical device specific identification information can include the identification of a specific medical device (i.e., a logical name or address, the IP address, or some other information identifying an infusion pump), or provide "look-up" information for retrieving the identification of a specific medical device. Likewise, patient specific identification information can include the identification of a specific patient (i.e., name, social security number, ID number, digital photograph and/or some other identifier) or provide "look-up" information for retrieving the identification of a specific patient. In addition, the medical device specific delivery information can be actual data required to operate the medical device or the general medical order information specific to the type of medical device (i.e., for an infusion pump, which could include start time for an infusion, rate of an infusion, and volume to infuse).

The method also retrieves at the first computer medical device specific delivery information based on the drug container specific identification information, transmits to the second computer from the first computer the medical device specific identification information and the medical device specific delivery information, and transmits the medical device specific delivery information from the second computer to the medical device. The medical device can have a medical device memory for storing the medical device specific delivery information for use in programming the medical device to deliver the medication to the patient. After at least one of the aforesaid transmitting steps, the method receives at the first computer patient specific identification information, and compares at least one of the received drug container specific identification information and the patient specific identification information to stored medication order information within a first memory associated with the first computer. The method further transmits a first medication delivery initiation signal to the second computer if the received drug container specific identification information and/or the patient specific identification information matches the stored medication order information within the first memory associated with the first computer, and, at least in part in response to receiving the first medication delivery initiation signal at the second computer, the second computer transmits a second medication delivery initiation signal to the medical device to initiate the delivery of the medication to the patient using the medical device specific delivery information previously received by the medical device.

In another embodiment, the first memory associated with the first computer further comprises a plurality of medical administration records (MARs), wherein at least one MAR comprises a medication order.

In another embodiment, the above comparing step is performed without using the patient specific identification information.

In another embodiment, the drug container specific identification information comprises at least one of patient identification information, medication identification information, universal identification information, medication order information, and/or medical device delivery information.

In another embodiment, the method receives at the first computer patient specific identification information from the input device prior to transmitting to the second computer from the first computer the medical device specific identification information and the medical device specific delivery information, and/or prior to transmitting the medical device specific delivery information from the second computer to the medical device.

In another embodiment, the method transmits the patient specific identification information from the first computer to the second computer prior to the above comparison step.

In another embodiment, the method transmits the patient specific identification information from the second computer to the medical device prior to the comparison step.

In another embodiment, the method receives from the second computer, in communication with the medical device, an availability state signal for the medical device, and, if the availability state signal for the medical device indicates that the medical device is available, then the method transmits the medical device specific delivery information to the medical device for programming the medical device to deliver the medication to the patient. The method can further compare at least one of the received drug container specific identification information and the patient specific identification information to stored medication order information stored within a first memory associated with the first computer, and transmit a first medication delivery initiation signal to the medical device if the received drug container specific identification information and/or the patient specific identification information matches the stored medication order information within the first memory. In one embodiment, these comparing and transmitting steps are only performed if the availability state signal for the medical device indicates that the medical device is available. In another embodiment, the method only transmits the medical device specific delivery information to the medical device if the received drug container specific identification information and/or the patient specific identification information matches the stored medication order information within the first memory. In a further embodiment, if the availability state signal for the medical device indicates that the medical device is not available, then the method prevents any transmission of the medical device specific delivery information to the medical device.

In another embodiment, the method generates at the second computer first key information and second key information, transmits from the second computer the first key information to the first computer, transmits from the second computer the second key information to the medical device, transmits from the first computer the first key information to the medical device along with the medical device specific delivery information, and compares at the medical device the first key information to the second key information. In one embodiment, if a match exists between the first key information and the second key information, then the method displays the medical device specific delivery information on a display of the medical device for review by a caregiver to confirm that at least the medical device specific delivery information is correct for the patient. In another embodiment, if a match exists between the first key information and the second key information, then the method operates the medical device according to the medical device specific delivery information. The first key information and/or the second key information can be an encrypted security token. The method can further transmit from second computer to the first computer the IP address of the medical device, if the availability state signal for the medical device indicates that the medical device is available. In one embodiment, the first computer and the first memory associated with the first computer do not maintain the IP address of the medical device. Alternatively, the first memory associated with the first computer can store the IP address of the medical device within a MAR for the patient for tracking to which medical device the medical device specific delivery information is transmitted.

In another embodiment, the first key information includes a time stamp, and the method compares at the first computer the time stamp to a first actual time. If the difference between the time stamp and the first actual time is less than a predetermined time criteria, then the method transmits from the first computer the first key information to the medical device along with the medical device specific delivery information to the medical device. The method can also transmit the time stamp to the medical device, and compare at the medical device the time stamp to an actual time. If the difference between the time stamp and a second actual time is less than the predetermined time criteria, then the method programs the medical device with the medical device specific delivery information.

In another embodiment, the second key information comprises a second time stamp, and the method compares at the medical device the first time stamp and the second time stamp to an actual time. If the difference between the first time stamp and the actual time, and if the difference between the second time stamp and the actual time, are both less than a predetermined time criteria, then the method programs the medical device with the medical device specific delivery information.

The present invention is also directed to a system for implementing the above and other methods, as well as a computer program product for operation within a medication management computer for implementing a least a portion of the above and other methods, for administering a medication to a patient using a medical device.

Other features and advantages of the invention will be apparent from the following specification taken in conjunction with the following drawings.

DESCRIPTION OF THE DRAWINGS

FIG. 6 is a screen shot of one embodiment of a delivery information input device for inputting identification information and/or confirming delivery programming code data.

DETAILED DESCRIPTION OF THE PREFERRED EMBODIMENTS(S)

Figure 1:
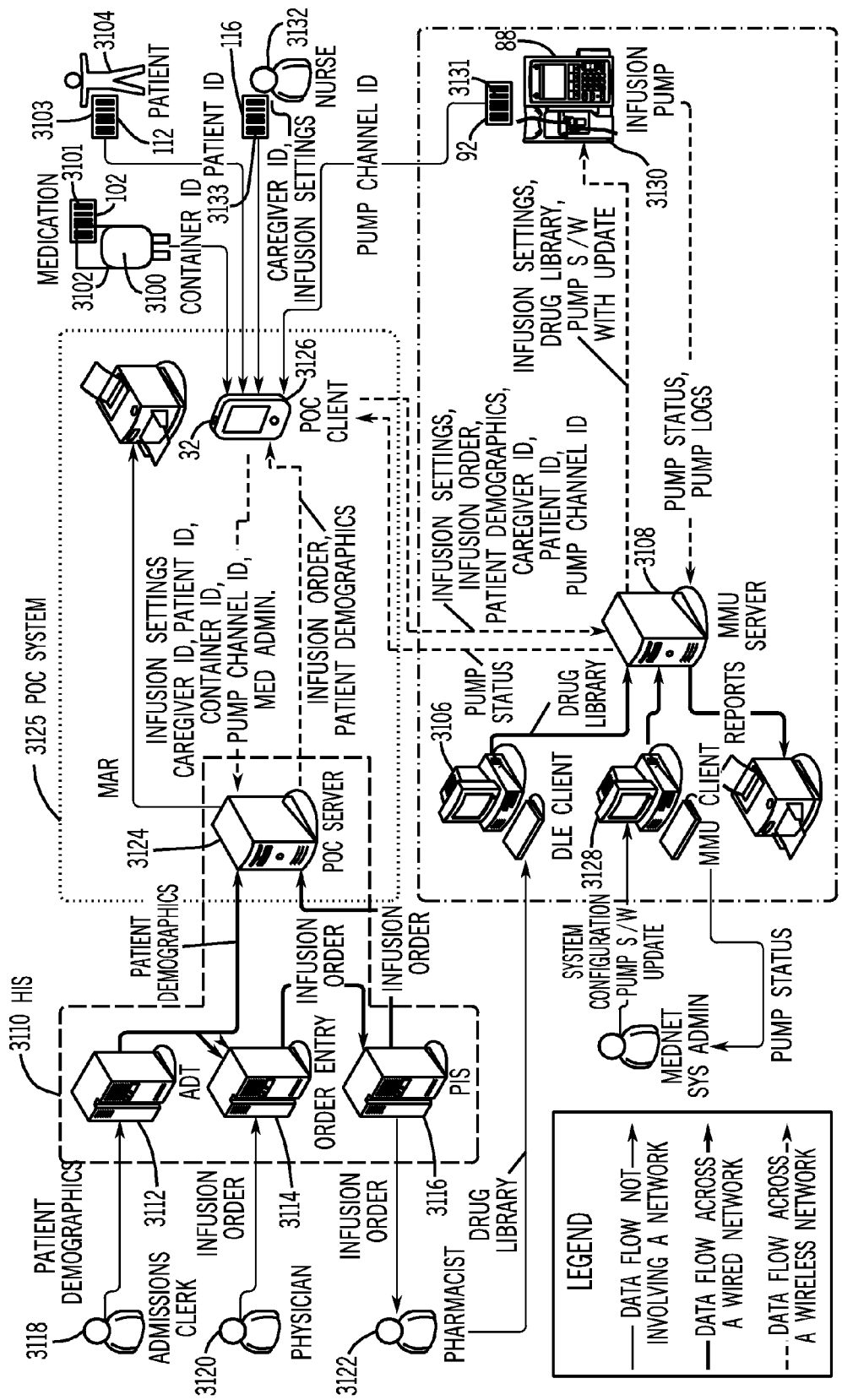
FIG. 1 is a schematic diagram showing a system and method for administering a medication to a patient using a point of care computer system comprising a POC server and a thick client input device according to one embodiment of the present invention.

In the figures and the description that follows, like reference numerals generally refer to like components or steps. In general, the system components described herein are described in greater detail in the commonly owned published U.S. patent application Ser. No. 20050144043, the disclosure of which is incorporated herein by reference in its entirety.

Definitions are provided below for some terms that appear in this description.

"Medical device" includes without limitation a pump, a monitor for monitoring patient vital signs or other parameters, or a diagnostic device. Typically a medical device is located in a particular physical location or clinical care area (CCA) within a hospital or some other environment. The medical device has a logical identifier or logical address and, when in contact with a communication network, has a network internet protocol or IP address if it is on a communication network "Pump" includes without limitation a device that acts upon a cassette, reservoir, vial, syringe, or tubing to convey medication or fluid to or from a patient (for example, without limitation, an enteral pump, an infusion pump, a patient controlled analgesia (PCA) or pain management medication pump, or a suction pump.

"Medication" as used herein is something that has a physiological impact on a person or animal, including but not limited to liquid or gaseous fluids, drugs or medicines, liquid nutritional products and combinations thereof. Medications that are delivered intravenously to patients are generally in liquid form, and are thus also referred to herein as "solutions".

Figure 2:
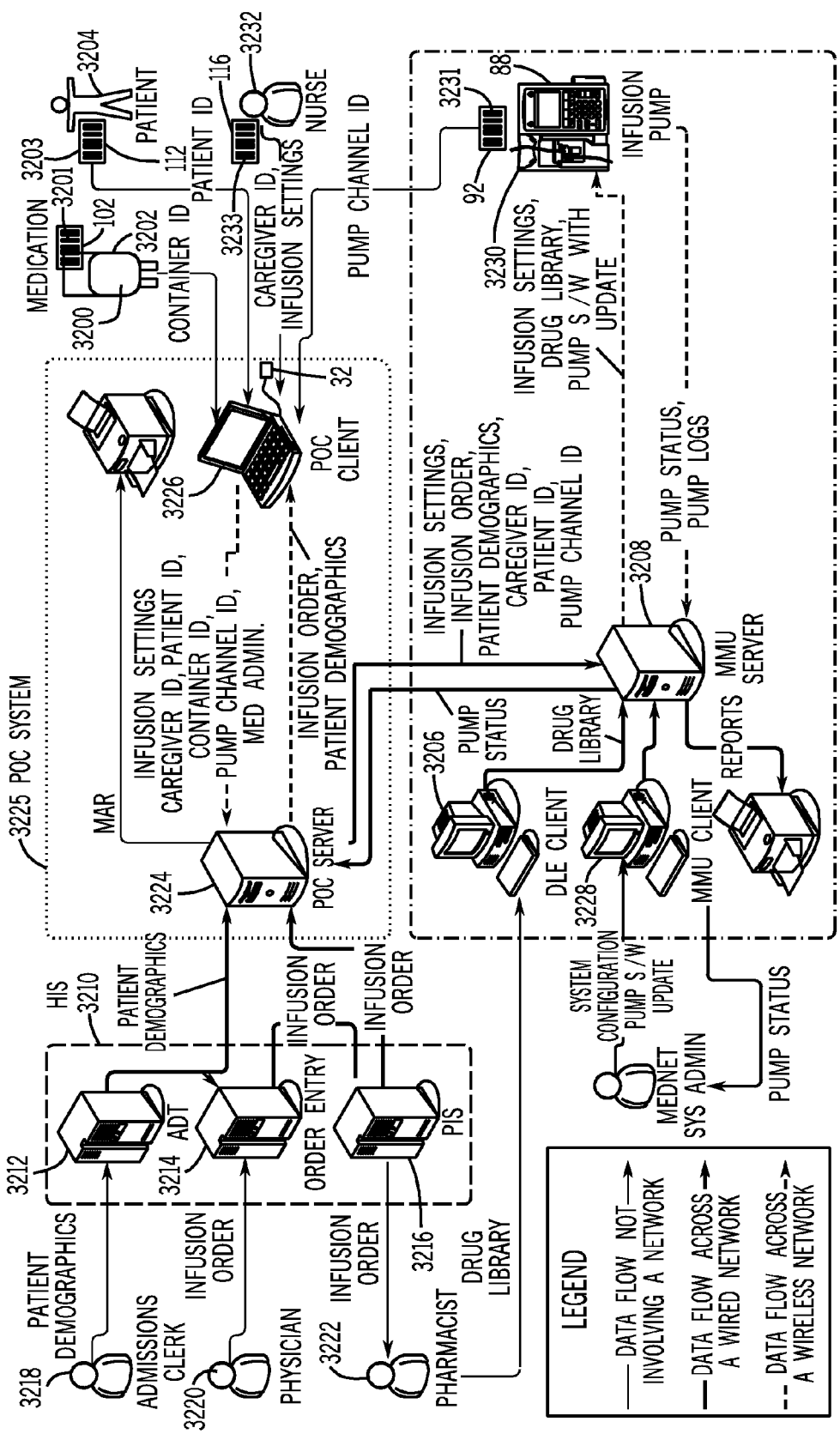
FIG. 2 is a schematic diagram showing a system and method for administering a medication to a patient using a point of care computer system comprising a POC server and a thin client input device according to one embodiment of the present invention.
Figure 3:
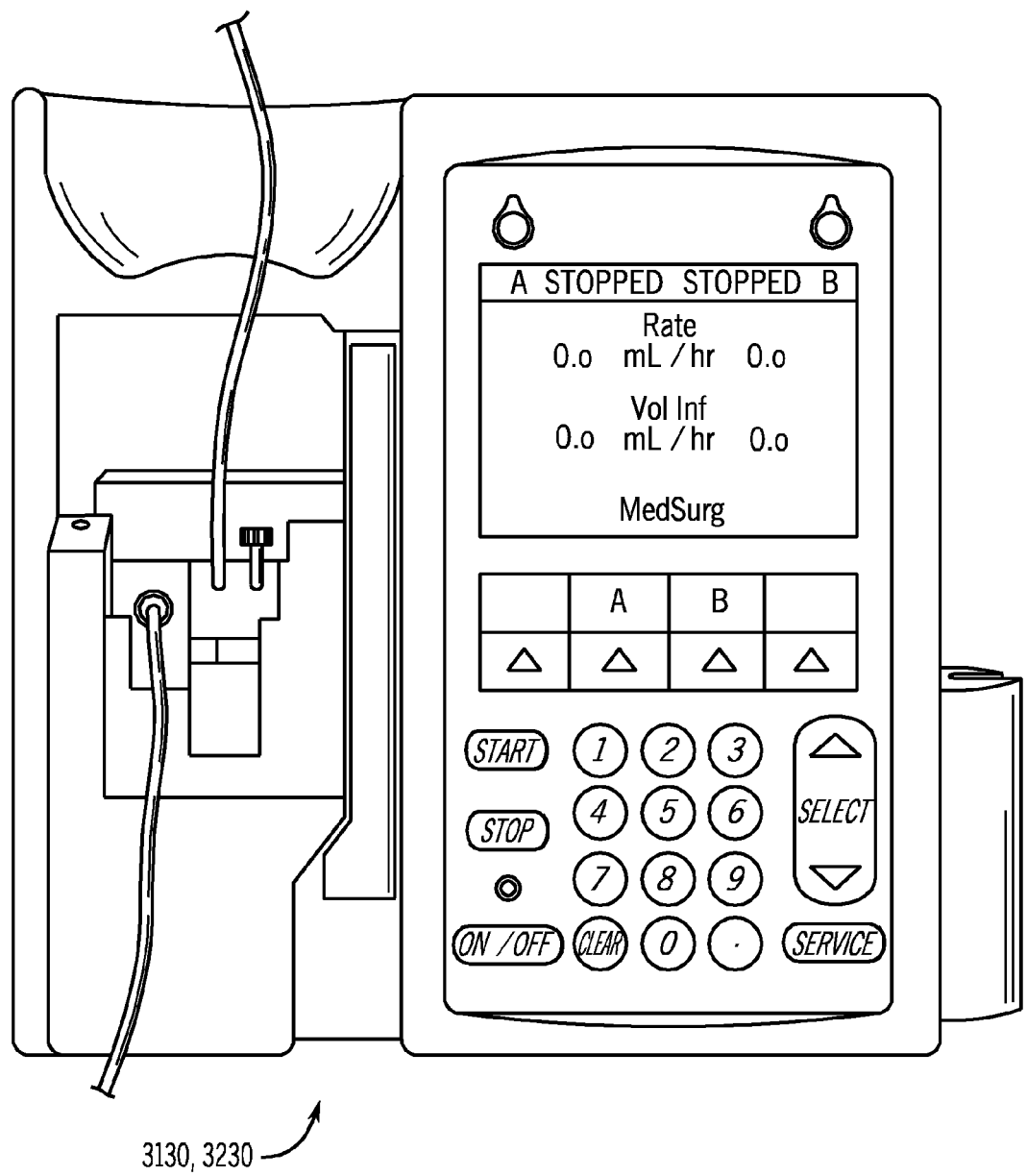
FIG. 3 is a front view of a medical device with a display and user interface, wherein the medical device is stopped and not displaying programmed infusion settings.

With reference to FIGS. 1 and 2, the medication management system (MMS) of the present invention includes a medication management unit (MMU) 3108, 3208 and a medical device 3130, 3230, typically operating in conjunction with one or more information systems or components of a hospital environment as further discussed below.

IV fluids/medications 3100, 3200 in containers 3102, 3202 can be administered to a patient 3104, 3204 through the system(s) shown in these FIGS. While the embodiments shown in FIGS. 1 and 2 utilize barcodes and a barcode reader as means for providing and inputting or reading machine readable information for identification or other purposes, those skilled in the art will appreciate from this description that other means for providing and reading information can be utilized. Machine readable indicia or identifying information can be provided by a radio frequency identification (RFID) tag, transmitter, or transponder and read by a radio frequency receiver or transceiver. Digital photography or imaging and scanning technology can be used. Human biometric data, including but not limited to skin/fingerprints, retina patterns, voice, etc can be recognized by an appropriate scanner or receiver. An input device 32 or identification receiver adapted to "read" or recognize such indicia can be provided.

The IV fluids/medications 3100, 3200 in barcode-identified containers 3102, 3202 can be given new or supplemental label(s) with a unique infusion order identifying barcode by the pharmacist according to hospital practice. In particular, the drug container specific identification information, such as barcoded information on the container 3102, 3202, can include patient identification information, such a patient name, patient number, or medical record number for which the medication has been prescribed, medication identification information, such as a medication name of the medication or solution within the IV bag or container 3102, 3202, universal identification information which can be created or assigned at the hospital, medical device delivery information, such as the operating parameters to use in programming an infusion pump to deliver the medication 3100, 3200 to the patient 3104, 3204, and/or medication order information, such as one or more of the above information items and/or other medication order information specific to a particular patient 3104, 3204, and which may be a part of a medication order for a particular patient. The IV fluids/medications 3100, 3200 in barcode-identified containers 3102, 3202 can be supplied to hospitals by various vendors, with preexisting unique barcode identifiers which include medication information and other information, such as National Disease Center (NDC) code, expiration information, drug interaction information, and other information.

The universal identification information on the container 3102, 3202 can be a unique medication order identifier that, all by itself, identifies the order associated with the container. Alternatively, the identification information on the container 3102, 3202 can be a composite patient/order code that contains both a patient ID (usually a medical record number) and an order ID (where the order ID is unique only within the context of that patient). Alternatively, the identification information on the container 3102, 3202 is merely a medication ID. Within a given hospital, all medications prepared or packaged for patients by the pharmacy will contain either a universally unique order ID or a composite patient/order ID, but generally not both within the same institution. The medication ID alone option is typically used only for medications that are pulled by the nurse directly from floor stock at the point of care.

The systems identified in FIGS. 1 and 2 can have a "drug library editor" or DLE computer 3106, 3206 such as a desktop, notebook, or server computer, with DLE software that runs on the DLE terminal, computer or workstation 3106, 3206 also shown as "DLE Client" in FIGS. 1 and 2. As described above, a medication management unit (MMU) or computer 3108, 3208, such as a server, has MMU software that is installed and runs on the MMU server 3108, 3208. The drug library and other databases can be stored on the MMU server 3108, 3208, a separate server, and/or in remote locations.

Hospital information systems (HIS) 3110, 3210 typically include one or more computers hard-wired together into a network 76 (FIGS. 5 and 5A) by cabling, interfaces and/or Ethernet connections. Alternatively wireless connections and communications can be used in whole or in part. Servers provide processing capability and memory for storage of data and various application programs or modules, including but not limited to a module for admissions-discharge-and-transfer (ADT) 3112, 3212, a computerized physician order entry (CPOE) module 3114, 3214, and a pharmacy information system (PhIS or PIS) module 3116, 3216. Hospital personnel, such as admission clerks 3118, 3218, physicians 3120, 3220, and pharmacists 3122, 3222, respectively, can be authorized to access these modules through client workstations connected to the servers in order to enter data, access information, run reports and complete other tasks.

Figure 5:
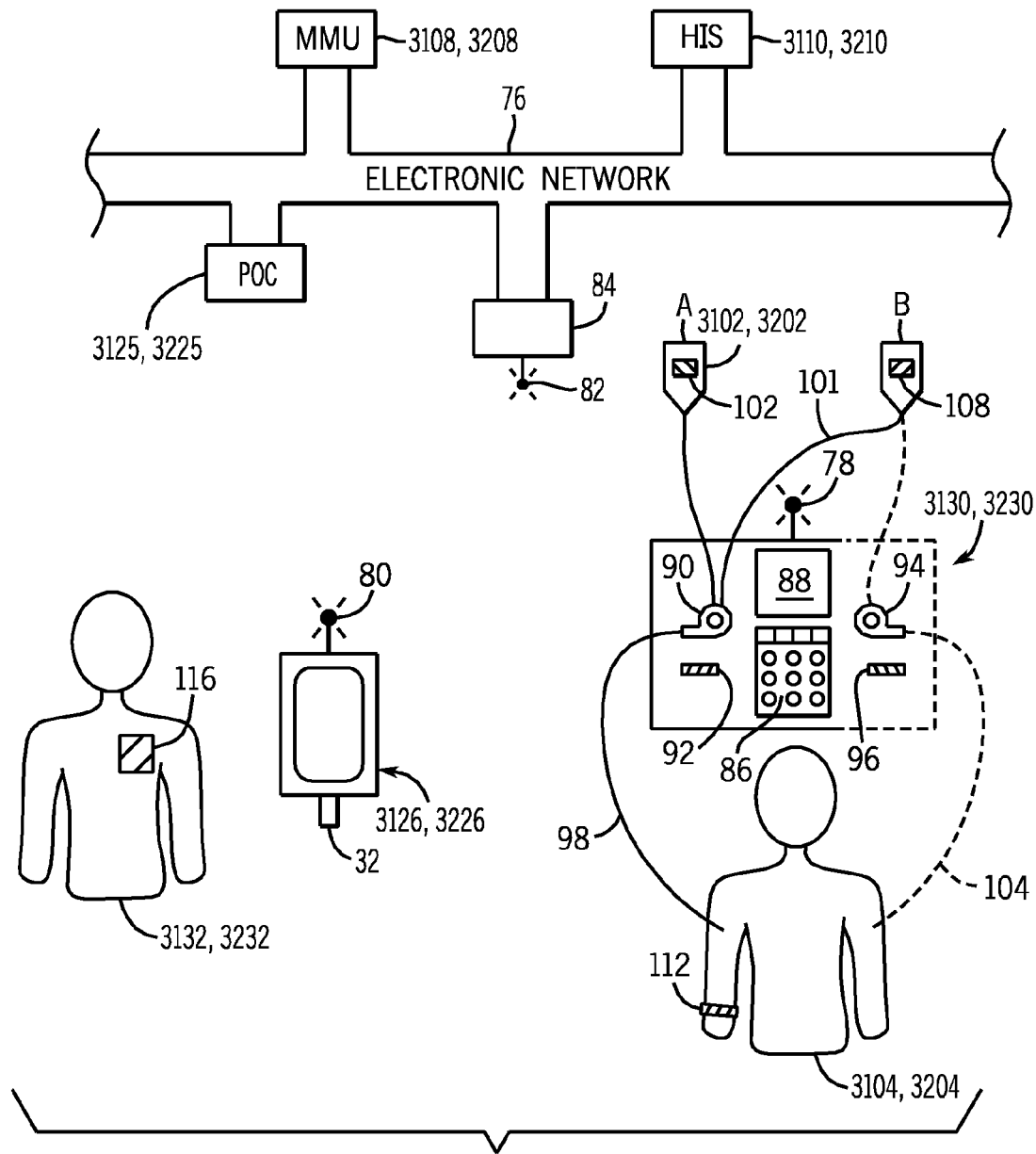
FIG. 5 is a simplified pictorial schematic diagram of a system for administering medication to a patient according to one embodiment of the invention.
Figure 5A:
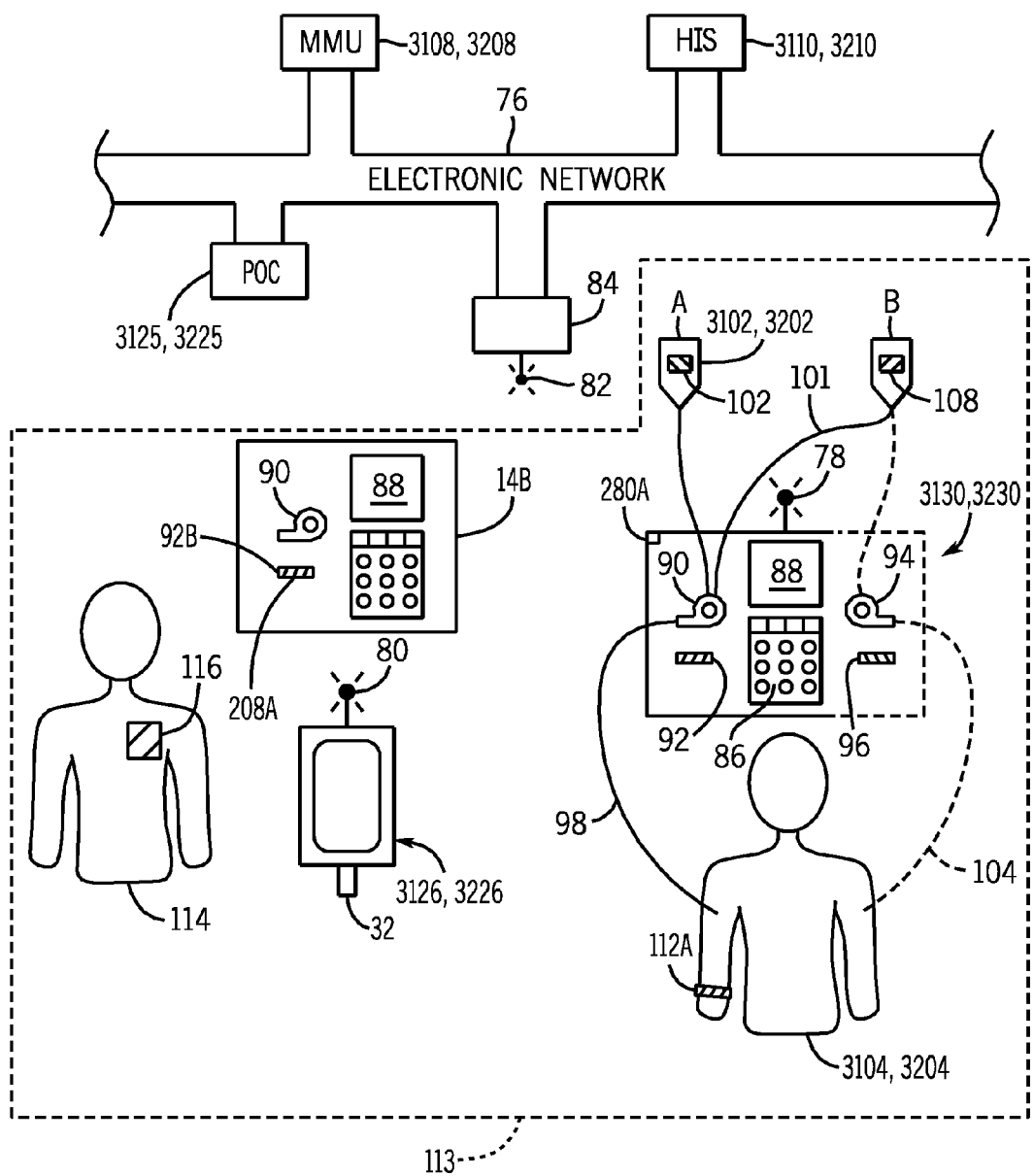
FIG. 5A is a simplified pictorial schematic diagram of a system for administering medication to a patient similar to FIG. 5 but shows the patient with a RFID wristband for auto-associating the patient and the medical device into a patient area network according to one embodiment of the invention.

In the embodiment shown in FIG. 1, the HIS 3110 can also include a point of care (POC) system 3125 including a server or POC computer 3124 (sometimes referred to as a barcode point of care server or computer), or the POC computer 3124 can be separate from the HIS 3110. In either case, the POC computer 3124 is typically hard-wired into the HIS network. The POC computer 3124 acts as part of a point of care (POC) system 3125 (sometimes referred to as the barcode point of care system or BPOC) and is able to wirelessly communicate through a plurality of wireless communication nodes located throughout the hospital, utilizing a wireless communications protocol, such as IEEE 801.11, IEEE 802.11, or Bluetooth. A wireless communication node 84 with an antenna 82 is typically included in each patient room or treatment area, as shown in FIG. 5. In the embodiment shown in FIG. 1, the POC computer 3124 wirelessly communicates with a portable "thick client" POC or input device 3126 carried by the caregiver. Referring to FIGS. 5 and 5A, the POC client device 3126 can be a personal digital assistant (PDA) that is equipped with or connected to a barcode scanner or other identification receiver/reader 32 such as a radio frequency (RF) receiver for receiving "RF tag" information when an RF tag is sufficiently near the RF receiver. The POC client device 3126 is referred to as a "thick client" because it has significant memory, display and processing capabilities of its own and can execute a variety of programs stored in its memory in some degree independently of the POC computer 3124.

In one embodiment of FIGS. 1 and 2, the MMU server 3108, 3208 is hard-wired to the DLE client desktop computer/workstation 3106, 3206 and to a MMU client computer/workstation 3128, 3228. Alternatively, the MMU and DLE client functions can be combined onto a single client computer/workstation or may reside together with the MMU server 3108, 3208 on a single combined MMU/DLE server. The MMU server 3108, 3208 preferably resides in a location remote from the patient's room or treatment area. For instance, the MMU server 3108, 3208 can reside in a secure, climate controlled information technology room with other hospital servers and computer equipment and its client terminals can be located in the pharmacy, biomedical engineering area, nurse station, or ward monitoring area. One MMU server 3108, 3208 can monitor, coordinate and communicate with many infusion pumps 3130, 3230. For example, in one embodiment, the MMU software running on the MMU server 3108, 3208 can support up to one thousand infusion pumps concurrently. In the thick client embodiment shown in FIG. 1, the MMU server 3108 need not be connected (hard-wired or wirelessly) to the hospital's Ethernet network backbone.

In the thick client embodiment of FIG. 1, the thick client PDA 3126 in the POC computer system 3125 may communicate in a peer-to-peer manner with the MMU server 3108. The MMU server 3108 interfaces or communicates wirelessly with the infusion pump 3130 and the PDA or POC client 3126 through the same wireless nodes 84 utilized by the POC system 3125 and a connectivity engine and antenna 78 (FIG. 5) on or in the infusion pump 3130. Communication between the MMU server 3108 and the POC system 3125 takes place through the PDA (POC client 3126)/MMU server 3108 wireless interface. Communication between the infusion pump 3130 and the POC client 3126 takes place through the MMU server 3108. Each thick POC client 3126 stores in an associated memory the URL address or internet protocol (IP) address of each MMU computer 3108 and each POC client 3126 communicates directly with such MMU computer 3108. The MMU computer 3108 stores in an associated memory both the logical ID and the network ID or Internet Protocol (IP) address of the infusion pump(s) 3130, such that only the MMU computer 3108 can communicate in a direct wireless manner with the infusion pump 3130. Alternatively, as will be described later, the MMU 3108 can provide the IP address and other information about the pump 3130 to the POC system 3125 to facilitate direct communication between the POC system 3125 and the pump 3130.

Regardless of whether the hospital uses the system architecture of FIG. 1 or FIG. 2, certain activities related to patient care typically take place in a hospital environment. Upon admission to the hospital, the admission clerk 3118, 3218 or similar personnel enters demographic information about each patient 3104, 3204 into an associated memory of the ADT computer or module 3112, 3212 of an HIS database stored in an associated memory of the HIS system 3110, 3210. Each patient 3104, 3204 is issued a patient identification wristband, bracelet or tag 112, 112A (FIGS. 5 and 5A) that includes an identifier 3103, 3203, such as a barcode or RFID tag for example, representing a unique set of characters, typically a patient ID or medical record number, identifying the patient, sometimes referred to as patient specific identification information. The wristband, bracelet or tag 112, 112A may also include other information, in machine readable or human-readable form, such as the name of the patient's doctor, blood type, allergies, etc. as part of the patient specific identification information.

The patient's doctor 3120, 3220 prescribes medical treatment by entering an order into the CPOE computer terminal or module 3120, 3220 within the HIS system 3110, 3210. The order, as prescribed, may specify a start time, stop time, a range of allowable doses, physiological targets, route, and site of administration. In the case of an order for infusion of fluids or medication, the order may be written in various formats, but typically includes the patient's name, patient ID number, a unique medication order or prescription number, a medication name, medication concentration, a dose or dosage, frequency, and a time of desired delivery. This information is entered into the memory of the CPOE computer 3124, 3224, and is stored in a memory associated with at least the POC server or computer 3124, 3224.

The medication order is also delivered electronically to the PIS computer 3116, 3216 in the pharmacy and is stored in an associated memory. The pharmacist 3122, 3222 screens the prescribed order, translates it into an order for dispensing medication, and prepares the medication or fluids with the proper additives and/or necessary diluents. As best seen in FIGS. 1, 2, 5 and 5A, the pharmacist 3122, 3222 prepares and affixes a label 102, 108 with drug container specific identifying information 3101, 3201 to the medication or drug container 3102, 3202. In one embodiment, the label only includes in machine-readable (barcode, RFID, etc.) form a unique sequentially assigned "dispense ID number" that can be tied or associated to the particular patient ID number and medication order number in the HIS 3110, 3210, PIS 3116, 3216 and/or POC computer 3125, 3225. In another embodiment, the label can include in machine readable form a composite identifier that includes an order ID and a patient ID, which is usually a medical record number. In another embodiment, the label does not include a patient ID at all in barcode or machine readable format but includes in machine readable form only a medication ID. This last embodiment may be useful for "floor stock" items that are commonly stocked in operating rooms, emergency rooms, or on a ward for administration on short notice with ad hoc or post hoc orders. In another embodiment, the label may include in machine readable and/or human-readable form medical device specific delivery information including but not limited to the dispense ID number, patient ID, drug name, drug concentration, container volume, VTBI, rate or duration, etc. Only two of the three variables VTBI, rate and duration must be defined as the third can be calculated when the other two are known. The labeled medication typically is delivered to a secure, designated staging location or mobile drug cart on the ward or floor near the patient's room or treatment area. The medication order pending dispensing or administration is posted to a task list in the HIS system 3110, 3210 and POC system 3125, 3225 and stored in an associated memory.

The nurse 3132, 3232 uses the input device 32 or identification receiver/reader associated with the POC client 3126, 3226 to scan the caregiver specific identification information 3133, 3233 or barcode on his/her caregiver identification badge 116 and enters a password, which logs the caregiver into the system and authorizes them to access a nurse's task list from the POC system 3125, 3225 through the POC client 3126, 3226. The information within the nurse's badge is sometimes referred to as the caregiver specific identification information herein. The nurse 3132, 3232 can see from the task list that IV drugs are to be administered to certain patients 3104, 3204 in certain rooms. The nurse 3132, 3232 obtains the necessary supplies, including medications, from the pharmacy and/or a staging area in the vicinity of the patient's room.

The following will be described with reference to FIG. 1, but may also be applicable to the embodiment of FIG. 2. The nurse 3132 takes the supplies to a patient's bedside, turns on the infusion pump 3130, verifies that the network connection icon on the pump 3130 indicates a network connection is present, selects the appropriate clinical care area (CCA) on the pump, and may mount the IV bag, container, or vial 3102 and any associated tube set as required in position relative to the patient 3104 and infusion pump 3130 for infusion. Using the identification receiver/reader 32 integral to the POC client PDA 3126, the nurse 3132 scans the barcode on the patient's identification bracelet 112. A task list associated with that particular patient will appear on the PDA 3126 screen. Presumably this task list, which may also include orders to give other forms of treatment or medication by other routes (oral, topical, etc.), is obtained from the HIS via the POC server 3124 and communicated wirelessly to the POC client PDA 3126. In one embodiment, the list is generated by matching the scanned patient ID with the patient ID for orders in memory within the POC server 3124. In another embodiment, as will be described below, the order information can be obtained by scanning the drug container specific identification information, for associated orders in memory within the POC server 3124, through the following step(s).

The nurse 3132 scans the medication barcode label 102 containing medication container specific identification information 3101 on the medication container 3102 with the PDA 3126. The PDA 3126 highlights the IV administration task on the task list and sends the scanned medication container specific identification information, such as dispense ID information, from the medication container 3102, to the POC server 3124, which uses the medication container specific identification information, such as the dispense ID, to pull together the rest of the order details and send them back to the PDA 3126. The PDA 3126 then displays an IV Documentation Form on its screen, as illustrated for example in FIG. 6. One side of the IV Documentation Form screen shows the order details as "ordered" and the other side is reserved for a status report from the infusion pump 3130. The status report from the infusion pump 3130 is transmitted to the PDA 3126 through the MMU server 3108, as will be described below. The lower portion of the IV Documentation Form screen gives the caregiver 3132 instructions (like to scan the infusion pump 3130 barcode) or tells whether the pump is running or stopped.

The nurse 3132 then scans the barcode label 92, 96 (FIGS. 5 and 5A) associated with the infusion pump 3130 (or pump channel if the pump is a multi-channel pump). The barcode label 92, 96 contains medical device specific identification information 3131, such as the logical name and/or logical address of the device or channel. The PDA 3126 then automatically bundles the information into a program pump request containing the "order details" and in one embodiment, without further interaction with the caregiver 3132, transmits this information wirelessly to the MMU server 3108. In another embodiment the POC server 3124 can transmit the order details to the MMU server 3108 via a hard-wired network connection.

The program pump request can includes the following information (in HIS/POC system format): a Transaction ID, which can include a Logical Pump ID, a Pump Compartment, a Pump Channel ID, a Reference Device Address, a Caregiver ID, a Caregiver Name, a Patient/Person ID (HIS identifier), a Patient Name, a Patient Birth Date & Time, a Patient Gender, a Patient Weight, a Patient Height, and an Encounter ID which can include a Room, a Bed, and a Building (including Clinical Care Area or CCA). The program pump request can also include Order Information or "order details", including an Order ID, a Start Date/Time, a Stop Date/Time, a Route of Administration, a Rate, a Duration of Infusion (Infuse Over), a Total Volume to be Infused (VTBI), an Ad Hoc Order Indicator, and Ingredients including HIS Drug Name or HIS Generic Drug Name, HIS Drug Identifier or HIS Generic Drug ID, Rx Type (Additive or Base), Strength w/units, and Volume w/units. The program pump request can further include Patient Controlled Analgesia (PCA) Orders Only information, such a PCA Mode-PCA only, Continuous only, or PCA and Continuous, a Lockout Interval (in minutes), a PCA Continuous Rate, a PCA Dose, a Loading Dose, a Dose Limit, a Dose Limit Time w/units, a Total Volume in vial, and Order Comments.

Upon receipt of a program pump request from the PDA 3126, the MMU 3108 validates the request by making sure that all infuser-required information has been provided and that any information provided, whether required or optional, is complete, within expected ranges and correctly formatted. For example, if height is included but is not a valid number or does not include units, the order would not be valid or complete. If the validation is successful, the MMU 3108 responds to the PDA 3126 with a program pump reply message. If the validation is unsuccessful, the MMU 3108 notifies the PDA 3126 via a program pump reply message and does not transform or send the order to the infusion pump 3130. Likewise, if the infusion pump 3130 is currently infusing, the MMU 3108 will reject the request and indicate with an error description in the program pump reply that the infusion pump 3130 is not ready to receive an order. The nurse 3132 must take some action to address the issue related to the infusion pump 3130, such as stopping the pump, retrying, or perhaps rescanning the correct pump channel on the infusion pump 3130 if the wrong channel was initially scanned. If the program pump reply message was affirmative, the PDA 3126 will repeatedly poll the MMU 3108 at regular intervals, for example every two seconds, with a read pump status request until the MMU 3108 is able to respond with a pump status reply based on a status message the MMU 3108 receives from the infusion pump 3130. The PDA 3126 also polls periodically for status updates as the infusion progresses.

The MMU 3108 identifies what type of infusion pump 3130 (standard or PCA) the program pump request is targeting, and then transforms the order into infuser specific details or settings. The MMU 3108 converts or reformats numbers received from the HIS system 3110 to the particular syntax, such as fixed-decimal point format for example, required by the infusion pump 3130. Rounding, conversion, or mapping of certain data may be needed to convert the information received from the PDA 3126 to settings the infusion pump 3130 can recognize, accept and utilize. Any data that is not required from the above listing can be left out of the request, then the MMU 3108 will transmit the incomplete order to the infusion pump 3130 and the caregiver 3132 can complete or modify the order at the infusion pump 3130, if desired.

The MMU 3108 maps or converts the wide range of expressions of units allowed by the HIS system 3110 or POC system 3125 for PDA 3126 requests into the much more limited set of units allowed in the MMU 3108 and infusion pump 3130. For example, the PDA 3126 request may express "g, gm, gram, or grams" whereas the MMU 3108 and/or infusion pump 3130 can accept "grams" only. Infusion pump 3130 delivery parameters or infusion pump 3130 settings are mapped or converted from corresponding order information or "order details" of the program pump request.

The MMU 3108 stores in an associated memory a mapping or translation table that keeps track of the logical ID of an infusion pump 3130 and the corresponding current network (static or dynamic) address (Internet Protocol (IP) address) or ID of the infusion pump 3130 on the network, which in this example is a wireless network. The MMU 3108 is able to translate or associate a given logical ID of the infusion pump 3130 with its network address in the translation table and provide the network IP address to the requesting POC system 3125 or device. The MMU 3108 also stores in an associated memory and/or can look up the drug library applicable to the scanned infusion pump 3130 and also converts the Drug ID and Strength from the pump program request into an index number of the medication at the desired strength or concentration from the drug library. The duration of the infusion comes from the POC system 3125 in hours and minutes and must be converted to just minutes for the infuser to recognize it. Volume or VTBI will be rounded to provide a value-specific and infuser-specific number of digits to the right of the decimal point. Units (of drug) will be converted to million units where appropriate. Patient weight is converted and either rounded according to infuser-specific rules or not sent to the infuser.

Once the MMU 3108 transforms the information from the program pump request into infusion pump settings or delivery parameters and other information in a format acceptable to the infusion pump 3130, the MMU 3108 wirelessly downloads a command message to the infusion pump 3130. If the infusion pump 3130 is not already equipped with the latest appropriate version of the hospital-established drug library, the MMU 3108 can also automatically download a drug library to the infusion pump 3130. The hospital-established drug library is maintained in a separate process undertaken by the biomedical engineer or pharmacist 3122 to place limits on the programming of the infusion pump 3130, as well as other infusion pump operating parameters such as default alarm settings for air in the line, occlusion pressure, etc. The drug library sets up acceptable ranges or hard and/or soft limits for various drug delivery parameters in the infusion pump 3130.

The MMU 3108 can also download to the infusion pump new versions, patches, or software updates of the infusion pump's internal operating system software. The infusion settings or delivery parameters and other information from the MMU 3108 is entered into the memory of the infusion pump 3130 and the infusion pump 3130 settings can automatically populate the programming screen(s) of the infuser, just as if the caregiver 3132 had entered the information and settings manually. The infusion pump 3130 screen populates with the name of the drug and drug concentration based on the drug library index number, patient weight (if applicable), rate, VTBI, and duration (only two of the last three variable are sent by the MMU 3108 because the pump 3130 can calculate the third from the other two). A return message of confirmation signal is sent to the MMU 3108 by the infusion pump 3130 to indicate that the command message has been received. At this point the caregiver 3104 may manually enter any additional infusion settings or optional information that was not included in the command message.

Figure 4:
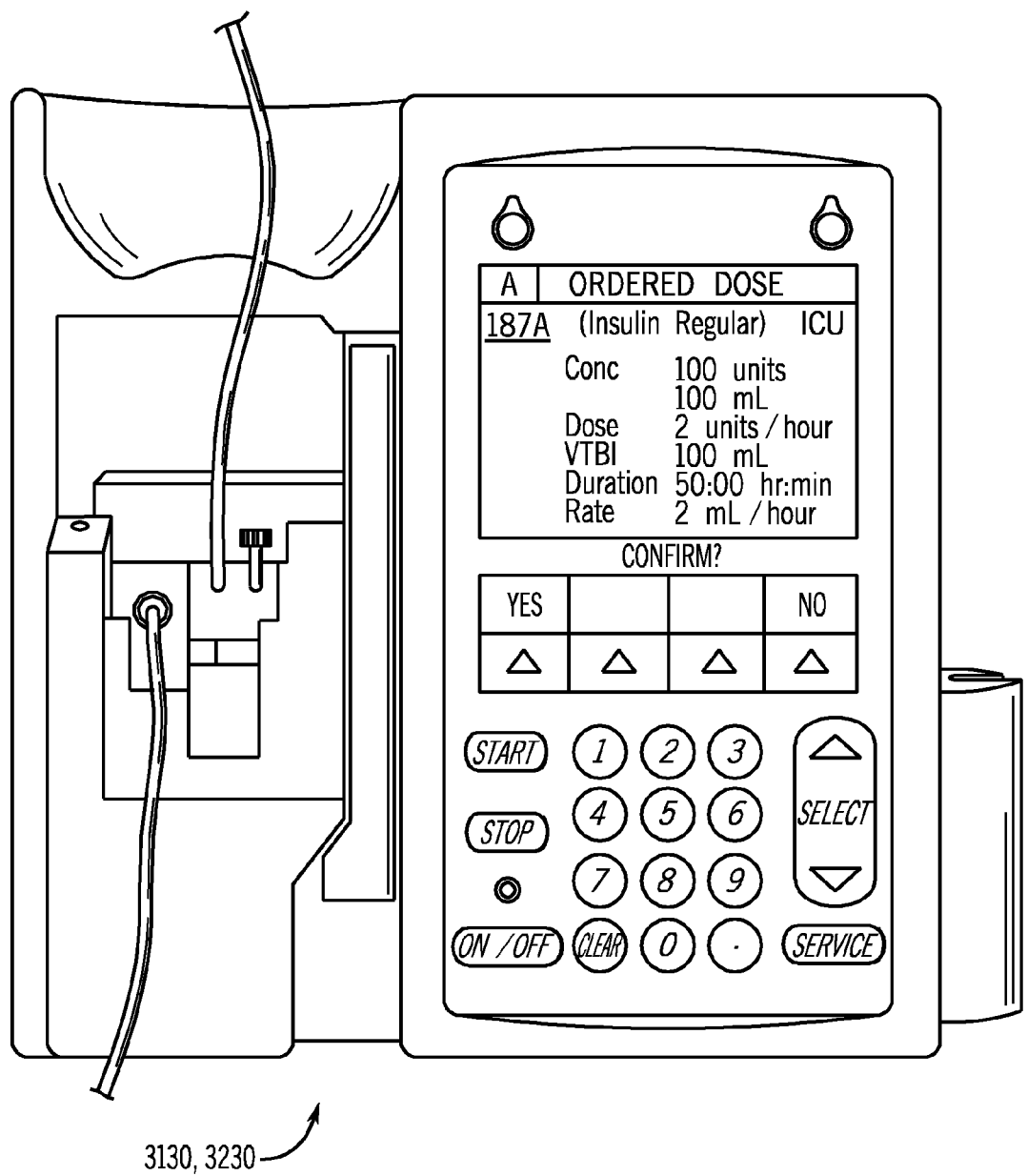
FIG. 4 is a front view of a medical device with a display and user interface, wherein the medical device is displaying downloaded infusion settings for confirmation or modification.

The infusion pump 3130 then prompts the caregiver 3132 to start the infusion pump 3130 by pressing the start button. When the caregiver 3132 presses the start button, a confirmation screen with the infusion settings programmed is presented to them for confirmation, as best seen in FIG. 4. When the caregiver 3132 presses the button to confirm, the infusion pump 3130 will begin delivering fluid according to the programmed settings. The infusion pump 3130 sends a status message to the MMU 3108 indicating that the infusion pump 3130 was successfully auto-programmed, confirmed and started by the caregiver 3132, and is now delivering fluid. The MMU 3108 continues to receive logs and status messages wirelessly from the infusion pump 3130 periodically as the infusion progresses or when alarms occur.

The MMU 3108 reports a portion of the initial status message to the PDA 3126 (in MMU format) to indicate that the infusion pump 3130 has been autoprogrammed and the caregiver 3132 has confirmed the settings. The MMU 3108 communicates to the PDA 3126 the actual Rate, VTBI and Duration. As shown in FIG. 6, these values are filled into the appropriate actual (pump) fields on the opposite side of the PDA IV Documentation Form screen from the corresponding "Ordered" values. A notation at the bottom of the PDA screen indicates that the infusion pump 3130 is running. The PDA 3126 will compare and give a visual, audio or other type of affirmative signal if the pump information matches or acceptably corresponds with the ordered information. An initial determination of whether the pump information matches the order can be done in the MMU 3108 and communicated to the PDA 3126. Alternatively, the POC server 3124 or the POC client PDA 3126 can make the necessary comparisons. If the pump information does not match the order, the PDA 3126 gives a visual, audio or other type of negative signal, which may include an error message. The nurse can also be prompted by the POC client or PDA 3126 at anytime during the process to enter the site of administration, and the PDA 3126 or the POC server 3124 matches that information as well. The same notification scheme or signals, as described above, can be followed for matching or mismatched conditions relating to the site of administration. In one embodiment, the site of administration is matched after the pump information is matched with the other order information.

The nurse 3132 is prompted to review and press a save button on the PDA 3126 if the order has been begun as desired or any variations are acceptable. In a separate subsequent step, the nurse electronically signs the record and presses a send button to send the information to the patient's electronic medication administration record (electronic MAR or EMAR).

Referring to FIG. 2, a thin client medication administration and management system and method is shown. From an HIS perspective, the structure is similar to the thick client POC structure described above, and shown in FIG. 1. However, the POC system 3225 includes POC server 3224 and a thin client notebook, tablet, handheld or PDA computer workstation 3226 that has little memory, computational power or ability to run its own programs. Instead, the client workstation or input device 3226 merely displays web pages it accesses from the server 3224 and relays input information to the POC server or computer 3224. The information is input through a user interface and/or an identification receiver/reader 32 integral with the POC client 3226 (FIG. 5) or connected to the POC client 3226 by a USB cord as shown in FIG. 2. Although the POC client 3226 has wireless WI-FL capability, in one embodiment, the POC client 3226 only communicates with the POC server 3224. The thin POC client 3226 may be attached to a mobile drug cart, mounted on a wall, or mounted at the bedside in the patient's room. The thin client computer 3226 at least temporarily stores data in a memory associated therewith in order to relay the data to the POC server 3224 or to display the data.

The POC server 3224 is typically hard-wired for communication with the MMU server 3208, but wireless communication is also a possibility due to the capabilities of the POC and MMU servers 3224, 3208.

The thin POC client 3226 of FIG. 2 is generally an input/pass-through/display device. In this embodiment, the POC client 3226 does not actually make any comparisons for five rights checking. The comparisons are made within the POC server 3224. The POC server 3224, rather than the POC client 3226, communicates directly with the MMU 3208.

In operation, the nurse 3232 scans his/her ID badge 116 and enters a password to access the system 3225 and an electronic MAR To-Do List that is displayed on the POC client 3226 screen. The nurse 3232 gathers the necessary supplies and medication, and then proceeds to the bedside of the patient 3204. The nurse 3232 places the IV bag 3202 or container and the associated tube set in position with respect to patient 3204 and the infusion pump 3230. The nurse 3232 turns on the infusion pump 3230, selects the clinical care area (CCA), and verifies that a wireless connection icon or indicator is present on the pump.

The nurse 3232 uses the identification (barcode) reader 32 on or attached to the POC client 3226 to scan the patient specific identification information 3203 on the patient's wristband 112. The wristband barcode includes a patient identification number in machine-readable format, and/or other information described above. The POC client 3226 displays the various physician orders and medication orders for the patient 3204.

The nurse 3232 scans the identifier, such as a barcode label 102 on the medication container or IV bag 3202 to obtain the medication specific identification information 3201. The barcoded label 102 on the medication container 3202 includes the medication specific identification information 3201, such as a unique number that is a combination of the patient ID and medication order number in a single block, as indicated above. The particular medication order associated with the medication container 3202 can retrieved from the medication specific identification information and/or from the POC server 3224, and displayed on the POC client 3226 screen along with an instruction for the caregiver to scan the IV pump 3230 (or channel if the pump is a multiple channel pump). In one embodiment, the nurse 3232 scans the label 92 or 96 on the infusion pump 3230 or pump channel and hits the "next" button on the POC client 3226. The order details are then retrieved from the POC server 3224 and displayed at the POC client 3226.

In one embodiment, nothing will happen until the nurse 3232 selects and enters the site (i.e., location on the body of the patient 3204) of the infusion from a dropdown menu on the order details screen. Consistent with the original order as prescribed by the physician 3220, the caregiver 3232 can modify the order and/or supply additional information such as rate, volume or other values which may be omitted in the order from the pharmacy. For example, if the physician's order is written as "titrate to affect" until blood pressure is below 200/100, a particular rate may not have been supplied with the order as translated by the pharmacy. After checking the patient's blood pressure or reviewing the latest measurements, the nurse 3232 may input a new or modified rate based on the specific patient condition. Recent laboratory results or values may also be relied upon to determine or adjust the order within the prescription of the physician.

In response to the caregiver hitting "next" after entering the site information and making any desired modifications to the order information, the POC server 3224 will download the order information to the MMU server 3208. A screen on the POC client 3226 indicates that the POC server 3224 is "sending settings to the IV pump", albeit through the MMU server 3208. The POC client 3226 screen instructs the nurse 3232 to go to the IV pump 3230 and confirm the settings on the display of the pump when they appear. The nurse 3232 also can change the settings by reprogramming the settings at the infusion pump 3230.

As in the "thick" client embodiment shown in FIG. 1, the MMU server 3208 must transform the order information from format stored in the memory associated with the POC server 3224 into infusion pump-recognizable settings. The MMU server 3208 also provides the latest appropriate drug library information for the infusion pump 3230 and converts the drug name and concentration information from the POC server 3224 into a drug library index number that the infusion pump 3230 understands. The MMU server 3208 and infusion pump 3230 communication and workflow is substantially the same as in the thick client embodiment. The nurse 3232 reviews the infusion pump 3230 settings on the display 88 of the infusion pump 3230, presses a start button, then is prompted with a confirmation screen to confirms the settings again as shown in FIG. 4. The nurse 3232 presses "yes" at a confirmation screen to actually start the infusion.

The infusion pump 3230 wirelessly communicates the start of the infusion and its infusion parameters back to the MMU 3208, which relays information such as the dose, VTBI, duration, rate and backpressure (distal pressure) to the POC server 3224 for display on the POC client 3226 display screen. Alternatively, the infusion settings or parameters can be relayed back to the POC client 3226 through the MMU 3208 and POC server 3224 at the press of the start button, and then updated when the "yes" button is pressed. The caregiver 3232 must hit "done" on the POC client 3226 screen to send this information to the patient's EMAR.

With reference to FIGS. 1 and 2, another embodiment of the medication administration system and method will now be described. As mentioned, the POC client 3126 (FIG. 1) or the POC computer 3224 (FIG. 2) is in communication with the MMU computer 3108, 3208. The POC server 3124, 3224 is also in communication with the POC client input device 3126, 3226. The nurse 3132, 3232 uses the POC client 3126, 3226 to scan his or her own badge 116, and the POC client 3126, 3226 processes and/or sends the caregiver specific identification information 3233 from the badge 116 to the POC computer 3224 for receipt by the POC computer 3224. The nurse 3132, 3232 uses the POC client 3126, 3226 to scan an identifier, such as a barcode label 102 for example, on the medication container 3102, 3202 to obtain medication or drug container specific identification information 3101, 3201 on the identifier, and the POC client 3126, 3226 processes and/or sends the drug container specific identification information to the POC computer 3124, 3224 for receipt by the POC computer 3124, 3224. The nurse 3132, 3232 uses the POC client 3226 to scan an identifier, such as a barcode label 92 for example, on the infusion pump 3130, 3230 or a channel of the pump to obtain medical device specific identification information 3131, 3231 on the identifier, and the POC client 3126, 3226 processes and/or sends the medical device specific identification information to the POC computer 3124, 3224 for receipt by the POC computer 3124, 3224.

Using the drug container specific identification information, the POC computer 3124, 3224 finds or retrieves from its own memory or a memory associated with the POC computer 3124, 3224, the medication order information associated with the drug container specific identification information 3101, 3201, which contains medical device specific delivery information for use in programming the infusion pump 3130, 3230. The POC computer 3224 or the POC client 3126 sends or transmits the medical device specific identification information, such as the pump ID, the caregiver specific identification information, such as the nurse's ID, the order ID obtained or retrieved from one of the drug container specific identification information or from the associated medication order stored in the memory associated with the POC computer 3224 and/or the POC client 3126, and the medical device specific delivery information, such as the pump settings for the order, to the MMU computer 3108, 3208.

In addition to or separate from other actions or functions which the MMU computer 3108, 3208 may perform at this stage, the MMU computer transmits the medical device specific delivery information, such as the pump settings, to the infusion pump 3130, 3230. The infusion pump 3130, 3230 includes a medical device memory for storing the medical device specific delivery information for use in programming the infusion pump 3130, 3230 to deliver the medication 3100, 3200 to the patient 3104, 3204. The infusion pump 3130, 3230 stores the settings in the pump memory, but in one embodiment does not display the settings on the display 88 of the infusion pump 3130, 3230, and therefore the settings cannot be seen by the nurse 3132, 3232 when the settings are initially stored in the pump memory. Alternatively, the programmed settings may be displayed on the display 88 of the pump 3130, 3230, but with a large cautionary warning that the settings are merely preliminary. The infusion pump 3130, 3230 then transmits a confirmation signal to the MMU computer 3108, 3208 that the infusion pump 3130, 3230 received the medical device specific delivery information, such as the pump settings for performing the infusion for the patient 3104, 3204 with the medication 3100, 3200. Once the MMU computer 3108, 3208 receives this confirmation signal, the MMU computer 3108, 3208 transmits a confirmation signal to the POC computer 3124, 3224 and/or the POC client 3126, 3226 that the medical device specific delivery information was received by the infusion pump 3130, 3230.

Once the POC computer 3124, 3224 and/or the POC client 3126 receives this confirmation signal, the software running on one or more of the POC system 3125, 3225 computers is structured to transmit a request to the POC client 3126, 3226 to prompt the nurse 3132, 3232 to read or scan the identifier, such as a barcode, on the patient's identification wristband 112. Thus, at this point, the nurse 3132, 3232 uses the POC client 3126, 3226 to scan the identifier, such as a barcode on the patient wristband 112 to obtain patient specific identification information 3103, 3203 on the identifier, and the POC client 3126, 3226 processes and/or sends or transmits the patient specific identification information 3103, 3203 to the POC computer 3124, 3224 for receipt by the POC computer 3124, 3224.

After receipt of patient specific identification information, the POC computer 3124, 3224 and/or the POC client 3126 does a "right patient" check. Specifically, the POC computer 3124, 3224 and/or the POC client 3126 compares at least one of the received drug container specific identification information and the patient specific identification information to the stored medication order information within the memory associated with the POC computer 3124, 3224 and/or the POC client 3126. If the received drug container specific identification information and/or the patient specific identification information matches the stored medication order information within the memory, then the POC computer 3124, 3224 and/or the POC client 3126 transmits a medication delivery initiation signal to the MMU computer 3108, 3208, which tells the MMU computer 3108, 3208 to "start the infusion." If all other applicable checks occurring at the MMU computer 3108, 3208, as described within the present specification, are satisfied then the MMU computer 3108, 3208 transmits a second medication delivery initiation signal to the infusion pump 3130, 3230 to communicate to the infusion pump 3130, 3230 that it is "safe" to initiate the delivery of the medication to the patient 3104, 3204 using the medical device specific delivery information, such as infusion parameters, previously transmitted to and received by the infusion pump 3130, 3230.

Software running on the infusion pump 3130, 3230 will then consider it safe to display the medical device specific delivery information, such as the infusion parameters for the medication order for the patient, on the display 88 of the infusion pump 3130, 3230 (without any warning that the settings are merely preliminary), and will do so. The infusion pump 3130, 3230 can be programmed to force the caregiver 3132, 3232 to manually press one or more buttons or receive some affirmative indication from the caregiver 3132, 3232 that the medical device specific delivery information on the display 88 is confirmed as correct for that particular patient 3104, 3204 and that particular medication 3100, 3200, etc. As described in prior embodiments, the MMU computer 3108, 3208 receives infusion pump 3130, 3230 status information from the infusion pump 3130, 3230. The MMU computer 3108, 3208 transmits this infusion pump 3130, 3230 status information along to the POC computer 3124, 3224 and/or POC client 3126 for display on the POC client 3126, 3226. The MMU computer 3108, 3208 stores this information in a memory associated with the MMU computer 3108, 3208 before forwarding along to the POC computer 3124, 3224 and/or the POC client 3126, 3226. Alternatively, the MMU computer 3108, 3208 can store the infusion pump 3130, 3230 status information in an associated memory and wait until the POC system 3125, 3225 requests or polls the MMU computer 3108, 3208 to request the MMU computer 3108, 3208 to send the pump status information to the POC system 3225 for display on the POC client 3126, 3226, for viewing by the caregiver 3132, 3232.

With continued reference to FIGS. 1 and 2, another embodiment of the medication administration system and method will now be described. This further embodiment is similar to the previous described embodiment. However, instead of waiting to read the identifier on the wristband 112 of the patient 3104, 3204 until after the medical device specific delivery information is transmitted to the infusion pump 3130, 3230, the caregiver 3132, 3232 scans the patient wristband identifier just after scanning the identifier on his or her own caregiver badge 116. The nurse 3132, 3232 can scan the patient wristband 112 before scanning the nurse's badge 116 or even after scanning the identifier 102 on the medication container 3102, 3202. The order is not significant, except that the system and method can be arranged to comply with a set of tasks and steps which are comfortable for the caregiver 3132, 3232 to follow. Thus, after the nurse scans the identifiers on the caregiver badge 116, the patient wristband 112, the medication container 3102, 3202, and the infusion pump 3130, 3230, but not necessarily in any particular order except for ease of use by a caregiver 3132, 3232, using the drug container specific identification information 3101, 3201 from the drug container 3102, 3202, the POC computer 3124, 3224 and/or POC client 3126, 3226 finds or retrieves from the memory associated with the POC computer 3124, 3224 and/or the POC client 3126, 3226, the medication order associated with the drug container specific identification information, which contains medical device specific delivery information for use in programming the infusion pump 3130, 3230. The POC computer 3124, 3224 and/or the POC client 3126 then sends or transmits the medical device specific identification information, such as the pump ID, the caregiver specific identification information, such as the nurse's ID, the patient specific identification information, such as the patient ID, the order ID obtained or retrieved from one of the drug container specific identification information or from the associated medication order stored in the memory associated with the POC computer 3124, 3224 and/or POC client 3126, and the medical device specific delivery information, such as the pump settings for the order, to the MMU computer 3108, 3208.

In addition to or separate from other actions or functions which the MMU computer 3108, 3208 may perform at this stage, software running on the MMU computer transmits the medical device specific delivery information, such as the pump settings, and the patient specific identification information, such as the patient ID to the infusion pump 3108, 3230. The infusion pump 3130, 3230 stores this information in the pump memory, but does not display this information on the display of the infusion pump 3130, 3230, and therefore this information cannot be seen by the nurse 3132, 3232. The infusion pump 3130, 3230 then transmits a confirmation signal to the MMU computer 3108, 3208 that the infusion pump 3130, 3230 received the medical device specific delivery information and the patient specific identification information. Once the MMU computer 3108, 3208 receives this confirmation signal, the MMU computer 3108, 3208 transmits a confirmation signal to the POC system 3125, 3225, more specifically the computer 3124, 3224 and/or the POC client 3126, 3226 that the medical device specific delivery information and the patient specific identification information was received by the infusion pump 3130, 3230.

Once the POC computer 3124, 3224 and/or the POC client 3126 receives this confirmation signal, the software running on the POC computer 3124, 3224 and/or the POC client 3126 does a "right patient" check. Specifically, the POC computer 3124, 3224 and/or the POC client 3126 compares at least one of the received drug container specific identification information and the patient specific identification information to the stored medication order information within the memory associated with the POC computer 3224 and/or the POC client 3126, 3226. If the received drug container specific identification information and/or the patient specific identification information matches the stored medication order information within the memory associated with the POC computer 3124, 3224 and/or the POC client 3126, 3226, then the POC computer 3124, 3224 and/or the POC client 3126 transmits a medication delivery initiation signal to the MMU computer 3108, 3208, which tells the MMU computer 3108, 3208 to "start the infusion." If all other applicable checks occurring at the MMU computer 3108, 3208, as described within the present specification, are satisfied, then the MMU computer 3108, 3208 transmits a second medication delivery initiation signal to the infusion pump 3130, 3230 to communicate to the infusion pump 3130, 3230 that it is "safe" to initiate the delivery of the medication to the patient 3104, 3204 using the medical device specific delivery information, such as infusion parameters, previously transmitted to and received by the infusion pump 3130, 3230.

Software running on the infusion pump 3130, 3230 will then consider it safe to display the medical device specific delivery information, such as the infusion parameters for the medication order for the patient, on the display of the infusion pump 3130, 3230, and will do so. The infusion pump 3130, 3230 can be programmed to force the caregiver 3132, 3232 to manually press a button or receive some indication from the caregiver 3132, 3232 that the medical device specific delivery information on the display is correct for that particular patient 3104, 3204 and that particular medication 3100, 3200, etc. As described in prior embodiments, the MMU computer 3108, 3208 receives infusion pump 3130, 3230 status information from the infusion pump 3130, 3230. The MMU computer 3108, 3208 transmits this infusion pump 3130, 3230 status information along to the POC computer 3124, 3224 and/or the POC client 3126 for display on the POC client 3126, 3226. The MMU computer 3108, 3208 stores this information in a memory associated with the MMU computer 3108, 3208 before forwarding along to the POC system 3125, 3225.

Alternatively, the MMU computer 3108, 3208 can store the infusion pump 3130, 3230 status information in an associated memory and wait until the POC computer 3124, 3224 and/or the POC client 3126, 3226 requests the MMU computer 3108, 3208 to request the MMU computer 3108, 3208 to send the pump status information to the POC computer 3124, 3224 and/or the POC client 3126 for display on the POC client 3126, 3226, for viewing by the caregiver 3132, 3232.

With continued reference to FIGS. 1 and 2, another embodiment of the medication administration system and method will now be described. However, for the purposes of this embodiment, in addition to the infusion pump 3130, 3230 communicating directly with the MMU computer 3108, 3208, the infusion pump 3130, 3230 also communicates directly with the POC computer 3124, 3224 and or the POC client 3126, 3226, which can be referred to as a peer to peer arrangement. In this embodiment, the MMU computer 3108, 3208 can be considered as a "marriage" broker, supplying an availability state signal or marrying a computer of the POC system 3125, 3225 to an infusion pump 3130, 3230 when the infusion pump is "available" for performing an infusion function with a patient 3104, 3204. The status and availability of the infusion pumps 3130, 3230 is tracked by the MMU computer 3108, 3208. Communication from the pump 3130, 3230 to the POC system 3125, 3225 is routed through the MMU server 3108, 3208 to allow for centralized monitoring of infusions by the MMU server 3130, 3230 while freeing up the POC system 3125, 3225 for other processing tasks.

In this embodiment, the caregiver uses the POC client 3126, 3226 to scan the identifiers on the caregiver badge 116, the patient wristband 112, the medication container 3102, 3202, and the infusion pump 3130, 3230 or channel thereof, but not necessarily in any particular order except for ease of use by a caregiver 3132, 3232. At this point the POC computer 3124, 3224, or even the POC thick client 3126, can perform one or more of the "five rights" checks, including comparing the received drug container specific identification information 3101, 3201 and/or the patient specific identification information 3103, 3203 to stored medication order information stored within the memory associated with the POC computer 3124, 3224 and/or POC client 3126. At this point, the nurse 3132, 3232 can review the medical device specific delivery information through the POC client 3126, 3226 and make any changes deemed necessary by the nurse 3132, 3232. The medical device specific delivery information 3131, 3231 can also be checked by, or against information which is stored in, the MMU computer 3108, 3208, in a manner similar to prior embodiments, such as for drug-drug interaction, dosing limits, and/or other checks. Alternatively, these comparisons and checks can be performed later in the process of the present embodiment.

The POC computer 3124, 3224 and/or the POC client 3126 then transmits a request to the MMU computer 3108, 3208 for permission to communicate with the infusion pump 3130, 3230 which has been scanned by the nurse 3132, 3232. This request is performed at least because the infusion pump 3130, 3230 may already be in communication in another server-client relationship with the POC server 3124, 3224 and/or the POC client 3126, or turned off, out of communication, or the infusion pump 3130, 3230 may be communicating with a separate POC sever or other system, or may be operating an infusion to the same patient or another patient. Thus, for preventing interruption of other communications and operations, and for other understandable safety reasons, the MMU computer 3108, 3208 determines if the infusion pump 3130, 3230 is available to communicate with the POC computer 3124, 3224 and/or the POC client 3126 and receive the medical device specific delivery information. If the MMU computer 3108, 3208 determines that the infusion pump 3130, 3230 is not available, the MMU computer 3108, 3208 transmits a non-available state signal to the POC computer 3124, 3224 and/or the POC client 3126, 3226, and the nurse 3132, 3232 is prevented from proceeding further with the infusion procedure or workflow. If the MMU computer 3108, 3208 determines that the infusion pump 3130, 3230 is available, then the MMU computer 3108, 3208 generates and transmits an available state signal for the medical device 3130, 3230. In one embodiment, the available state signal can include key information such as an encrypted security token which is generated by the MMU computer 3108, 3208. The key information can alternatively be separate from the available state signal. The MMU computer 3108, 3208 then transmits the key information, such as an encrypted security token, along with the IP address of infusion pump 3130, 3230 to the POC computer 3124, 3224 and/or the POC client 3126, 3226. The MMU computer 3108, 3208 also transmits the key information, such as an encrypted security token to the infusion pump 3130, 3230. Each key information, such as an encrypted security token can include an age or have an age associated therewith, which after a predetermined amount of time, such as two minutes, will time out or expire and prevent the key information, such as an encrypted security token from being useable. In one embodiment, each time the key information, such as an encrypted security token is used within a communication, the age can be reset or renewed. Alternatively, the key information, such as an encrypted security token can have a time stamp created at the time of generation by the MMU computer 3108, 3208, which can be used compared against an actual time of day when the key information, such as an encrypted security token is attempted to be used. The comparison of the time stamps to the time of day can be performed at the POC computer 3124, 3224, the POC client 3126, 3226 and/or at the infusion pump 3230, based on time of day tracking at these devices. The infusion pump 3130, 3230 can have a real-time clock for this purpose.

If an available state signal, which can include key information for the infusion pump 3130, 3230 is received by the POC computer 3124,3224 and or the POC client 3126, 3226, the POC computer 3124, 3224 and/or the POC client 3126, 3226 can then retrieve the medical device specific delivery information and any other information that may be needed by the infusion pump 3130, 3230, and transmit this information along with the key information, such as an encrypted security token to the infusion pump 3130, 3230, using the IP address of the infusion pump 3130, 3230 received from the MMU computer 3108, 3208, for use in programming the infusion pump 3130, 3230 to infuse the medication 3100, 3200 to the patient 3104, 3204. If the POC computer 3124, 3224 has not performed any or completed "five rights" checking, the POC computer 3124, 3224 and/or the POC client 3126, 3226 will compare the received drug container specific identification information and/or the patient specific identification information to the stored medication order information within the memory associated with the POC computer 3124, 3224 and/or POC client 3126, before retrieving and transmitting the medical device specific delivery information to the infusion pump 3130, 3230 along with the key information, such as an encrypted security token, for use in programming the medical device 3130, 3230 to deliver the medication 3100, 3200 to the patient 3104, 3204. Alternatively, the POC computer 3124, 3224 and/or the POC client 3126, 3226 can transmit the medical device specific delivery information to the infusion pump 3130, 3230 without the key information, such as an encrypted security token and wait until after "five rights" checking is completed by the POC computer 3124, 3224 and/or the POC client 3126, 3226 before transmitting the key information to the infusion pump 3130, 3230.

In one embodiment, if the medical device specific delivery information is transmitted to the infusion pump 3130, 3230 without the security token, the infusion pump 3130, 3230 will automatically reject the medical device specific delivery information, and will prevent the infusion pump 3130, 3230 from being programmed utilizing the medical device specific delivery information retrieved by the POC computer 3124, 3224 and/or the POC client 3126, 3226. In one embodiment, the infusion pump 3130, 3230 compares encrypted security tokens received from the POC computer 3124, 3224 (and/or the POC client 3126, 3226) and from the MMU computer 3108, 3208 to determine if the infusion pump 3130, 3230 should be programmed according to the received medical device specific delivery information. If the key information, such as the encrypted security tokens do not match or correspond in a predetermined way, the infusion pump 3130, 3230 will automatically reject the medical device specific delivery information, and will prevent the infusion pump 3130, 3230 from being programmed utilizing the medical device specific delivery information sent by the POC system 3125, 3225 (retrieved by the POC computer 3124, 3224 and/or the POC client 3126, 3226). In one embodiment, until the above checks occur at the infusion pump 3130, 3230, the medical device specific delivery information will be stored in the infusion pump memory and will not be displayed until after such checks occur and are affirmative.

The infusion pump 3130, 3230 status information functionality can be performed according to embodiments described above, through the MMU computer 3108, 3208 and to the POC computer 3124, 3224 and/or the POC client 3126, 3226. Alternatively, the infusion pump 3130, 3230 status information can be sent directly to the POC computer 3124, 3224 and/or the POC client 3126, 3226 for display on the display of the POC client 3126, 3226, or when the POC system 3225 (computer 3124, 3224 and/or POC client 3126, 3226) requests status from the infusion pump 3130, 3230. Even if the infusion pump 3130, 3230 status information is to be sent directly to the POC system 3125, 3225, the infusion pump 3130, 3230 status information can also be sent directly to the MMU computer 3108, 3208 according to prior embodiments described herein.

The present embodiment prevents the MMU computer 3108, 3208 from having to process as much information, as compared to prior embodiments. The present embodiment also improves the liveliness of the auto-programming workflow by using peer-to-peer communications between POC system 3125, 3225 and the infusion pump 3130, 3230, circumventing MMU message queuing and any inherent disadvantages associated therewith.

Figure 7A:
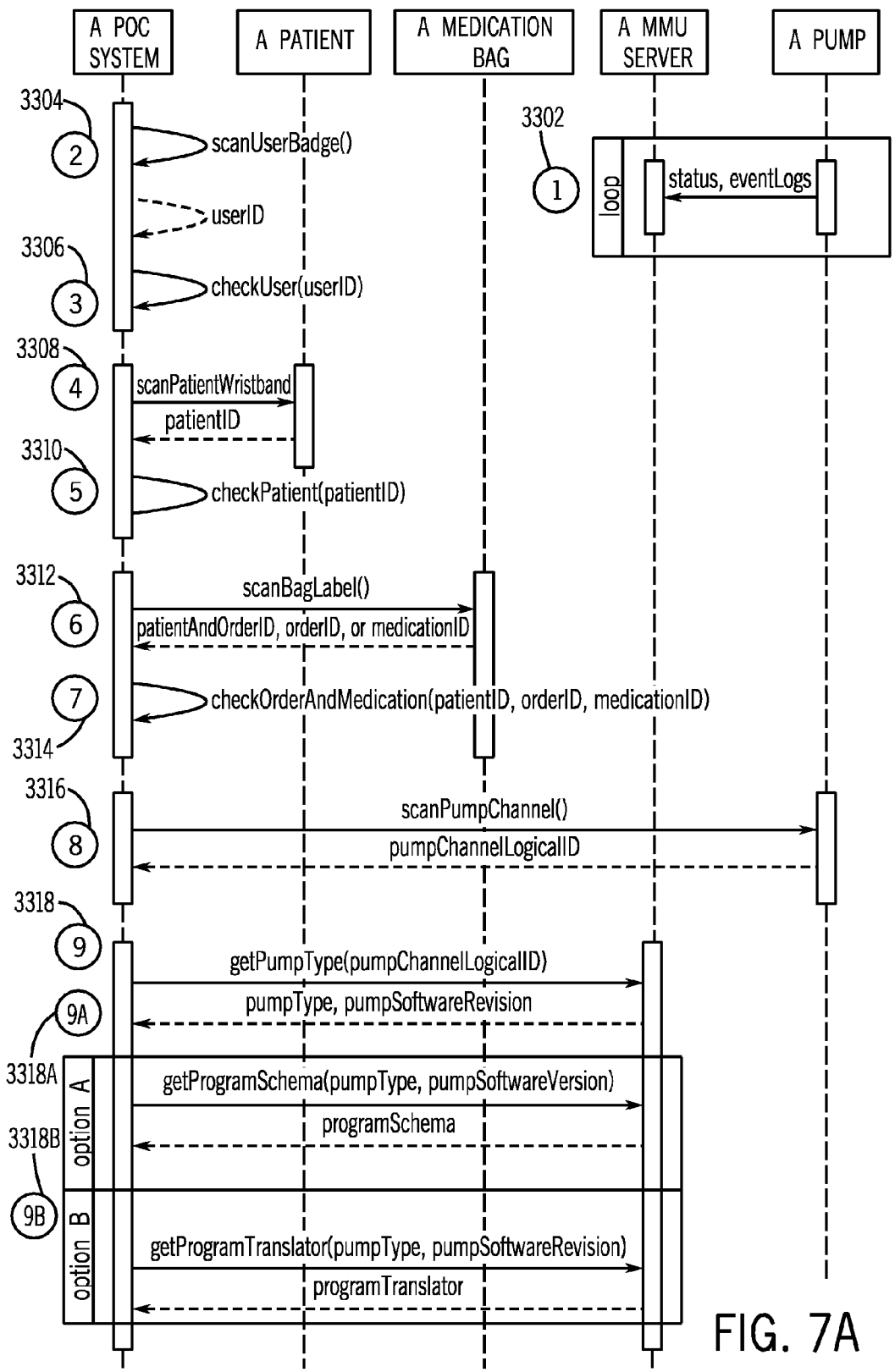
FIG. 7A is a flow chart showing a method for administering a medication to a patient according to one embodiment of the present invention.
Figure 7B:
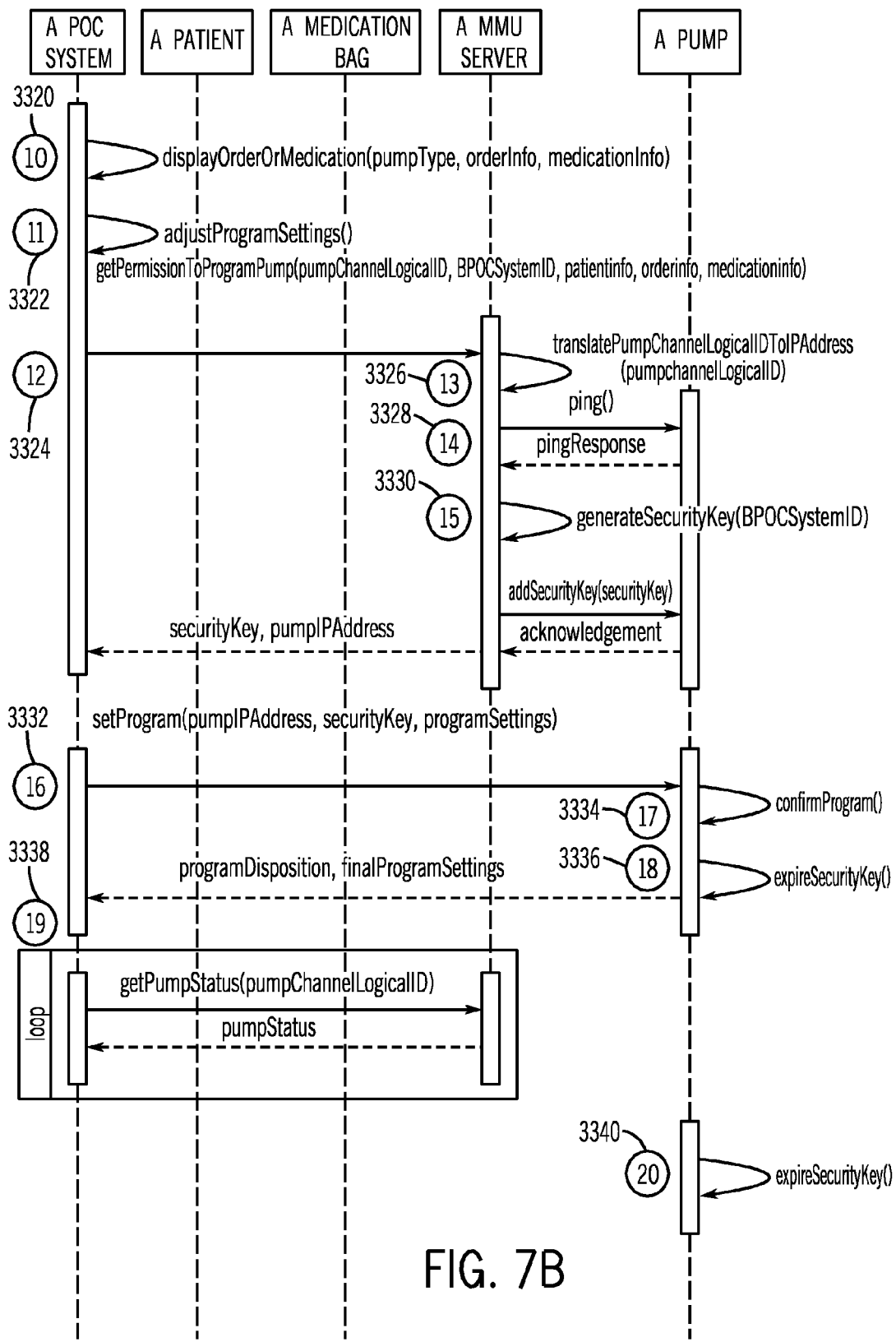
FIG. 7B is a continuation of the flow chart of FIG. 7A.

Referring to flowcharts of FIGS. 7A and 7B in addition to FIGS. 1 and 2, another embodiment of the system and method of administering a medication 3100, 3200 to a patient 3104, 3204 using an infusion pump 3130, 3230 is shown. Specifically, similar to the previous embodiment, when the POC system 3125, 3225 is auto-programming the infusion pump 3130, 3230, the POC system 3125, 3225, including the POC computer 3124, 3224 and/or the POC client 3126, 3226 requests the MMU 3108, 3208 for permission to program the infusion pump 3130, 3230. Once this permission is granted by the MMU computer 3108, 3208, the POC system 3125, 3225 communicates directly with the infusion pump 3130, 3230 without MMU computer 3108, 3208 intervention. In this embodiment, a first process step 3302 provides that the MMU computer 3108, 3208 continually receives asynchronous (i.e. unsolicited, un-polled) status messages and event logs from the infusion pump 3130, 3230 and stores this information in an associated memory for purposes of at least displaying infusion pump 3130, 3230 status and generating reports.

In a second process step 3304, as in prior embodiments, the nurse 3132, 3232 can start the workflow for automatically programming the infusion pump 3130, 3230 by using the POC system 3125, 3225 to scan the identifier on the nurse's ID badge 116. In a third process step 3306, the POC system 3125, 3225 determines if the nurse 3132, 3232 is a valid POC system 3125, 3225 user. The POC system 3125, 3225 may also require the nurse 3132, 3232 to enter a password, and/or other information.

In a fourth process step 3308, the nurse 3132, 3232 at the POC system 3125, 3225 then scans the identifier on the patient's wristband 112. In a fifth process step 3310, the POC system 3125, 3225 then looks up the patient 3104, 3204, at which time the POC computer 3124, 3224 and/or the POC client 3126, 3226 can retrieve the patient status, such as their recorded condition, present medications being taken, and/or any other information which may exist in that patient's EMAR, as well as retrieve the patient's medication orders, for administration.

In a sixth process step 3312, the nurse 3132, 3232 obtains the bag or container 3102, 3202 of medication 3100, 3200, and scans the identifier on the identification label 102 on the container 3102, 3202. In a seventh process step 3314, the POC system 3125, 3225 performs various checks on the order or medication typically ensuring that the medication was, in fact, ordered, that it is the correct time to deliver the medication, that the patient has no known allergies or intolerances toward the medication, that the medication will not interact adversely with another medication the patient is receiving, and/or other "five rights" and safety checks.

In an eighth process step 3316, the POC system 3125, 3225 determines that the medication is potentially "pump-able" and transmits a query to the POC client 3126, 3226 asking the nurse 3132, 3232 if the nurse wants to deliver the medication 3100, 3200 using an infusion pump 3130, 3230. The POC system 3225 can accept a yes/no response to the query, or the POC computer 3124, 3224 and/or the POC client 3126, 3226 can accept a response of the nurse 3132, 3232 actually scanning an identifier for an infusion pump 3130, 3230 channel. If the nurse 3132, 3232 scans the identifier of the infusion pump 3230 channel as the response, the POC system 3125, 3225 receives a pump channel logical ID from the scanned barcode identifier 92.

In a ninth process step 3318, the POC system 3125, 3225 transmits a request to the MMU computer 3108, 3208 for the type of infusion pump 3130, 3230 and the software revision for the infusion pump 3130, 3230 based upon the given logical ID of the pump/pump channel. At this point, the POC system 3125, 3225 can then utilize the information concerning the type of infusion pump 3130, 3230 and the software revision for the infusion pump 3130, 3230 to adjust or tailor the workflow, communications, and the user interface itself (on the POC client 3126, 3226 and elsewhere) so as to be appropriate for the type of infusion pump 3130, 3230 and the software revision for the infusion pump 3130, 3230 being used.

In another variant 3318A of the ninth step, the POC system 3125, 3225 may further include or transmit, concurrently with or separately from the pump type and software revision request, a request to the MMU 3108, 3208 to provide the pump's program schema (i.e., the syntax of the program messages it accepts) from the MMU 3108, 3208 for the infusion pump 3130, 3230 based on the given pump/pump channel logical ID and/or the pump type and/or software revision. The program pump schema is an XML schema that precisely defines the syntax for programs a particular pump 3130, 3230 will accept. In addition to defining the specific optional and required information, the schema can define the required characteristics of such information, including but not limited to format, maximum values, minimum values, decimal point placement, and number of digits or characters. The POC system 3125, 3225 can then use this information to ensure that the program it sends to the pump 3130, 3230 has the correct syntax. In other words, the pump program schema is basically a template that the POC system 3125, 3225 can use as a guide to transform its medical device specific delivery information or medication order information into information that is usable to program a particular pump 3130, 3230 of a given type and software revision.

In another variant 3318B of the ninth step, the POC system 3125, 3225 may further include or transmit, concurrently with or separately from the pump type and software revision request, a request to the MMU computer 3108, 3208 to provide an actual software module or program (i.e., an executable software package) which the POC system 3125, 3225 can run in its process space (POC computer 3124, 3224 or POC client 3226) that will automatically translate the infusion pump program from a device-neutral to a device-specific format. The program is translator script or executable code written in Java or another suitable programming language, which when executed by the POC system 3125, 3225 will automatically convert, translate, or transform the medical device specific delivery information or medication order information from the POC system 3125, 3225 into information that is usable to program the pump 3130, 3230. The translator program can be tailored for the particular POC system 3125, 3225 in question by utilizing a POC system ID such as described below and is, of course, tailored to the specific target infusion pump 3130, 3230.

In an optional tenth process step 3320, the POC system 3125, 3225 displays medication order and/or medication 3100, 3200 information on the display of the POC client 3126, 3226, which can be tailored for the particular pump 3130, 3230 type. The pump type or other information about the pump, such as software revision, schema, or translation identifiers can also be displayed on the POC client 3126, 3226. The medication and medication order information can be in POC system format or in infuser setting format.

In an optional eleventh process step 3322, the nurse 3132, 3232 at the POC system 3125, 3225 can then adjust the infusion pump settings through the POC client 3126, 3226. In one embodiment, if a medication ID was scanned from the identifier on the label 102 on the medication container 3102, 3202, and the identifier does not include an order ID, then the nurse 3232 may have to enter the infusion pump 3230 settings from scratch on the POC client 3126, 3226. The nurse 3232 then confirms the settings indicating that the infusion should proceed to be programmed into the pump 3130, 3230.

In a twelfth process step 3324, the POC system 3125, 3225 transmits a requests to the MMU computer 3108, 3208 requesting permission to program the infusion pump 3130, 3230. With the request, the POC system 3125, 3225 transmits the pump channel's logical ID, the POC system's ID, at least some patient information (e.g. name, number, room, bed, etc.) at least some order information (e.g., order ID, parameters for infusion, etc.) and some medication information (e.g., medication ID, medication name, etc.). The MMU computer 3108, 3208 first ensures that the POC system 3125, 3225 is known based on the POC system ID provided.

In a thirteenth process step 3326, the MMU computer 3108, 3208 attempts to translate the pump channel's logical ID into a physical IP address, using medical device information stored in a memory associated with the MMU computer 3108, 3208. The MMU computer 3108, 3208 has in its memory (as part of the status information it receives on a periodic or looping basis in step 3302 from various infusion pumps it is in communication with) an up-to-date look up or translation table of static pump logical IDs and network pump IDs or IP addresses. In a fourteenth process step 3328, the MMU computer 3108, 3208 then transmits a signal which "pings" the infusion pump 3130, 3230 to make sure the infusion pump 3130, 3230 is online and available for an infusion. It is possible that the infusion pump 3130, 3230 may not be available because it may be currently infusing a different patient, the pump channel may already be in use, etc. This transmission can also request the infusion pump 3130, 3230 to retrieve the very latest status information from the infusion pump 3130, 3230 and transmit this status information back to the MMU computer 3108, 3208 as a part of its ping response.

In a fifteenth process step 3330, assuming the pump channel is available for programming an infusion, the MMU computer 3108, 3208 generates a security key that the POC system 3125, 3225 will use to identify itself (the POC system 3125, 3225) to the infusion pump 3130, 3230. In one embodiment, the POC system ID is included in the security key or token, which can be encrypted. In a sixteenth process step 3232, the MMU computer 3108, 3208 transmits the security key to the infusion pump 3130, 3230. The infusion pump 3130, 3230 maintains list of security keys within the infusion pump 3130, 3230 memory. Every security key can have a finite predetermined lifetime, such as five minutes for example. If the infusion pump 3130, 3230 does not receive any communication from the appropriate POC system 3125, 3225 for which the respective security key was assigned and stored within the memory of the infusion pump 3130, 3230, within lifetime of the stored security key, the security key automatically expires. Conversely, every time the infusion pump does receive a communication relating to a particular POC system 3125, 3225 and thus to a particular security key stored in the infusion pump memory, the security key is renewed, and the finite lifetime is reset to its original time or some other increased finite time. The infusion pump 3130, 3230 then transmits to the MMU computer 3108, 3208 an acknowledgement or confirmation signal, and the MMU computer 3108, 3208, in turn, transmits the security key and IP address to the POC system 3125, 3225.

In a seventeenth process step 3334, the POC system 3125, 3225 then transmits the medical device specific delivery information, such as the program settings, directly to the infusion pump 3130, 3230 using the IP address of the infusion pump 3130, 3230, including transmission of the security key to the infusion pump 3130, 3230. In one embodiment, the POC system 3125, 3225 prompts the nurse 3132, 3232 through the POC client 3126, 3226 to step over to the infusion pump 3130, 3230 to confirm the program settings on the display 88 of the pump. The program settings can be transmitted to the infusion pump 3130, 3230 in the pump's device-specific format.

In an eighteenth process step 3336, the infusion pump 3130, 3230 receives the program settings and displays the program settings on the display 88 of the infusion pump 3130, 3230. As mentioned, the nurse 3132, 3232 can confirm the program settings on the pump 3130, 3230. Once confirmation occurs, and the infusion pump 3130, 3230 is programmed, the infusion pump 3130, 3230 then expires the security key since the infusion pump 3130, 3230 has been successfully programmed. Alternatively, the infusion pump 3130, 3230 could be designed so as not to immediately expire the security key. In this alternative, it would be possibly to resend program settings in the event of communication failure or other error conditions. The infusion pump 3130, 3230 could always use the security key to ensure that it receives a complete program at most once. In either case, the infusion pump 3130, 3230 transmits a confirmation or disposition signal to the POC system 3125, 3225, including information indicating that the program settings were accepted as-is, accepted with edits, or rejected—along with, if accepted, the final program settings.

In a nineteenth process step 3338, the POC system 3125, 3225 may then poll the MMU computer 3108, 3208 for status information about an infusion pump channel using the channel's logical ID. In a twentieth process step 3340, which can be a part of other steps, an infusion pump 3130, 3230 will automatically expire a security key when the key's lifetime elapses without any communication from a POC system using the key.

Figure 8A:
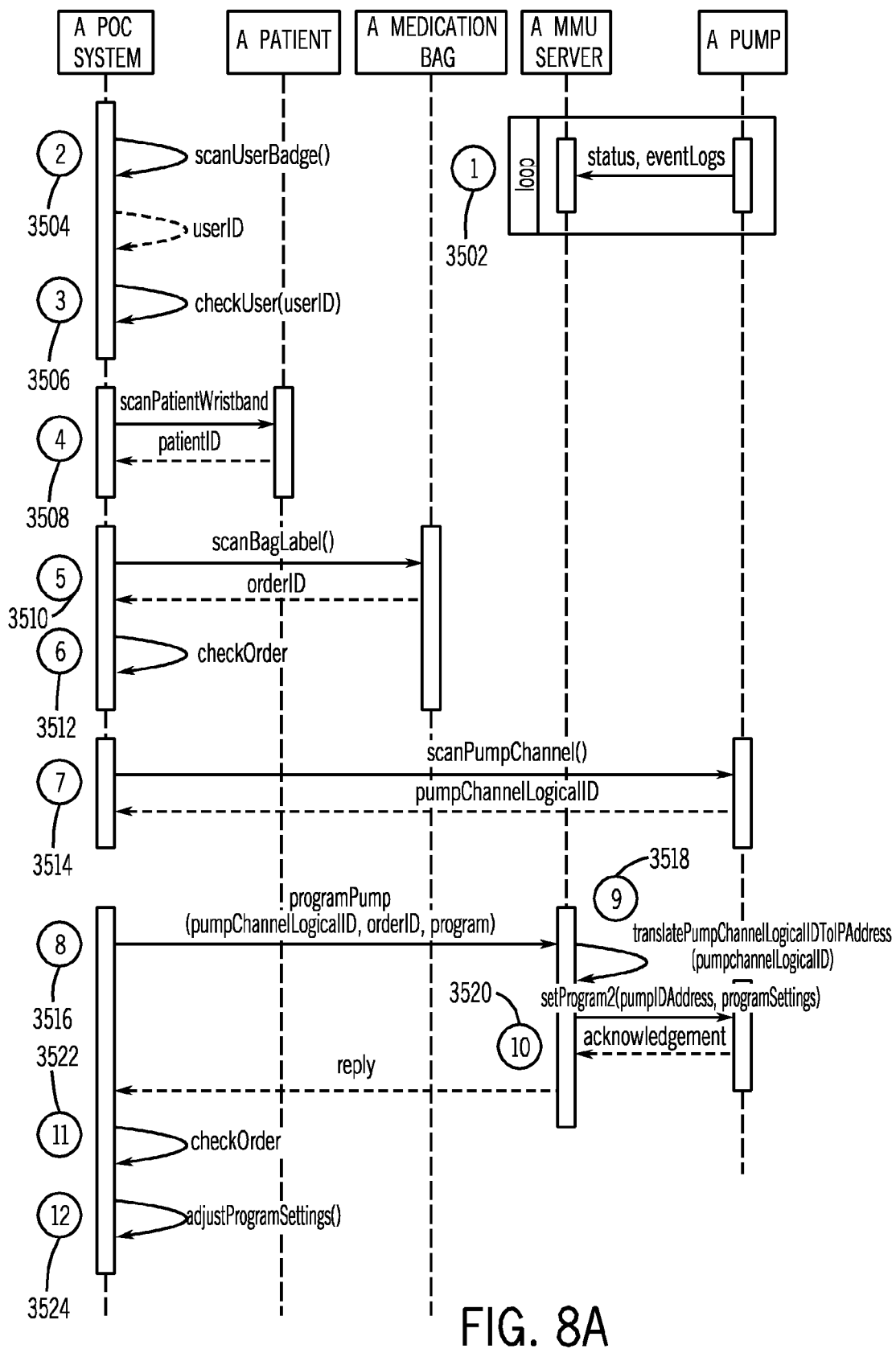
FIG. 8A is a flow chart showing a method for administering a medication to a patient according to one embodiment of the present invention.
Figure 8B:
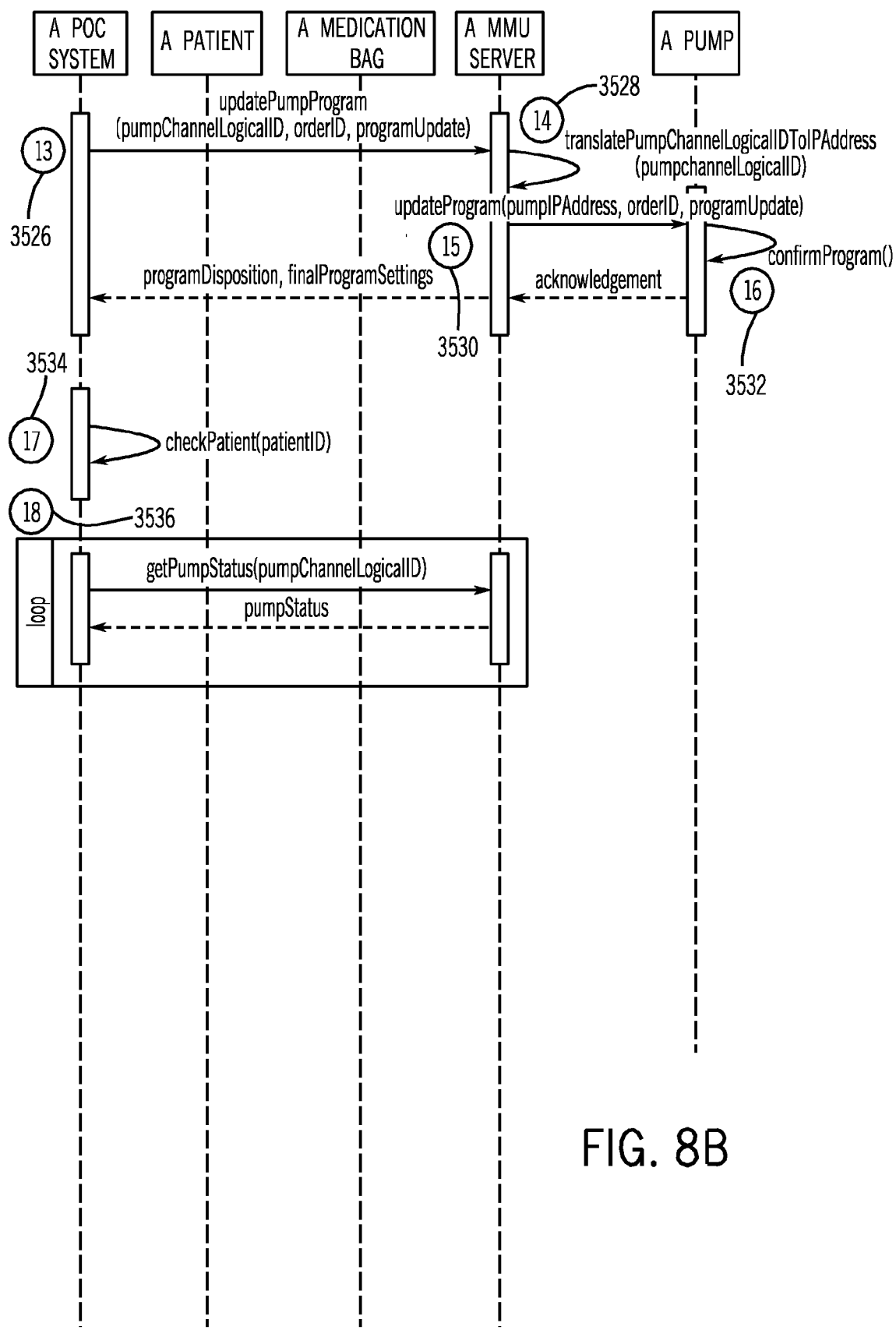
FIG. 8B is a continuation of the flow chart of FIG. 8A.

Referring to flowcharts of FIGS. 8A and 8B in addition to FIGS. 1 and 2, another embodiment of the system and method of administering a medication 3100, 3200 to a patient 3104, 3204 using an infusion pump 3130, 3230 is shown. Specifically, this MMU server mediated embodiment is substantially similar to the previous embodiments where the medical device specific delivery information, including a program, is transmitted to the infusion pump 3130, 3230 from the POC system 3125, 3225 through the MMU computer 3108, 3208 before the patient 3104, 3204 is positively identified. In the present embodiment, as described below a subsequent updated program can be transmitted to the infusion pump 3130, 3230, if necessary.

In this embodiment, a first process step 3502 provides that the MMU computer 3108, 3208 continually receives asynchronous (i.e. unsolicited, un-polled) status messages and event logs from the infusion pump 3130, 3230 and stores this information in an associated memory for purposes of at least displaying infusion pump 3130, 3230 status and generating reports.

In a second process step 3504, as in prior embodiments, the nurse 3132, 3232 can start the workflow for auto-programming of the infusion pump 3130, 3230 by using the POC system 3125, 3225 to scan the identifier on the nurse's ID badge 116. In a third process step 3506, the POC system 3125, 3225 determines if the nurse 3132, 3232 is a valid user of the POC system 3125, 3225. The POC system 3125, 3225 may also require the nurse 3132, 3232 to enter a password, and/or other information. In a fourth process step 3508, the nurse 3132, 3232 at the POC system 3125, 3225 then scans the identifier on the patient's wristband 112. As will be understood based on the description below, the scanning of the identifier on the patient's wristband 112 alternatively can be delayed until after programming the pump when the identifier is actually needed for a "right patient" comparison.

In a fifth process step 3510, the nurse 3132, 3232 obtains the container 3102, 3202 of medication 3100, 3200 and then scans the identifier on the identification label 102 on the container 3102, 3202. The container ID can be a universally unique order ID so that the POC system 3125, 3225 can retrieve information about the associated medication order without having to scan the patient ID on the patient wristband 112 or rely on such patient ID information for comparison purposes. In a sixth process step 3512, the POC system 3125, 3225 performs various checks on the order including checking the order ID, as in prior embodiments, but does not make any checks relative to the patient, as the patient wristband may not yet have been scanned to determine the identify of the patient. Alternatively, these order related checks can be deferred until after the tenth process step 3520, described below.

In a seventh process step 3514, the POC system 3125, 3225 determines that the medication is potentially "pump-able" and either transmits a query to the POC client 3126, 3226 asking the nurse 3132, 3232 if the nurse wants to deliver the medication using an infusion pump 3130, 3230. The POC computer 3124, 3224 and/or the POC client 3126, 3226 can accept a yes/no response to the query or the POC system 3125, 3225 can accept a response of the nurse 3132, 3232 actually scanning an identifier 92 for an infusion pump 3130, 3230 or pump channel thereof. If the nurse 3132, 3232 scans the identifier 92 of the infusion pump 3130, 3230 channel as the response, the POC system 3125, 3225 receives a pump channel logical ID from the scanned barcode.

In an eighth process step 3516, the POC system 3125, 3225 transmits the pump channel's logical ID, the order ID, and the medical device specific delivery information, such as the program (i.e. order) settings to the MMU computer 3108, 3208, and communicates to the MMU computer 3108, 3208 that the MMU computer 3108, 3208 should send the medical device specific delivery information to the infusion pump 3130, 3230. In a ninth process step 3518, the MMU computer 3108, 3208 translates the pump channel's logical ID into an IP address, as in prior embodiments.

In a tenth process step 3220, the MMU computer 3108, 3208 transmits the medical device specific delivery information, including the program to the infusion pump 3130, 3230. The infusion pump 3130, 3230 stores this information in the pump memory for use in programming the pump to infuse the medication into the patient. The infusion pump 3130, 3230 can send a confirmation to the MMU computer 3108, 3208 that it received this information. The MMU computer 3108, 3208 then transmits to the POC system 3125, 3225 that the medical device specific delivery information has been sent to the infusion pump 3130, 3230.

In an eleventh process step 3522, the nurse 3132, 3232 checks the order information and in a twelfth step 3524 can adjust and confirm the medical device specific delivery information, such as the program settings through the POC system 3125, 3225, such as through the POC client 3126, 3226.

In a thirteenth process step 3526, the POC system 3125, 3225 transmits an updated medical device specific delivery information, such as an updated pump program including the pump channel's logical ID, the order ID, and a program update to the MMU computer 3108, 3208. If the nurse 3132, 3232 made no changes to the medical device specific delivery information, then this transmission is an "empty trigger" to the MMU computer 3108, 3208, which merely instructs the MMU computer 3108, 3208 to transmit to the infusion pump 3130, 3230 to continue with the previously sent medical device specific delivery information/program. The POC system 3125, 3225 might display a message, such as through the POC client 3126, 3226, instructing the nurse 3132, 3232 to review and confirm the medical device specific delivery information on the display 88 of the infusion pump 3130, 3230.

In a fourteenth process step 3528, the MMU computer 3108, 3208 again translates the logical ID into an IP address. In a fifteenth process step 3530, the MMU computer 3108, 3208 transmits the updated medical device specific delivery information, such as the updated program to the infusion pump 3130, 3230, instructing the infusion pump 3130, 3230 to actually implement the medical device specific delivery information. In a sixteenth process step 3532, the infusion pump 3130, 3230 receives the medical device specific delivery information and displays the medical device specific delivery information on the display 88 of the infusion pump 3130, 3230. The nurse 3132, 3232 confirms the medical device specific delivery information at the infusion pump 3130, 3230 by performing some affirmative act at the infusion pump 3130, 3230. The infusion pump 3130, 3230 transmits to the MMU computer 3108, 3208 a disposition or acknowledgment including how the medical device specific delivery information was disposed of (accepted as is, accepted with edits, or canceled), and the MMU computer 3108, 3208 transmits this information to the POC system 3125, 3225 along with the final medical device specific delivery information settings.

In a seventeenth process step 3534, the POC system 3125, 3225 performs a "right patient" check as a part of the "five rights" checking. At this time any other checking on the order (e.g. right time, allergies, drug-drug interactions, etc.) can also be performed.

In an eighteenth process step 3536, the POC system 3125, 3225 may then poll the MMU computer 3108, 3208 for status information about an infusion pump channel using the channel's logical ID.

Figure 9A:
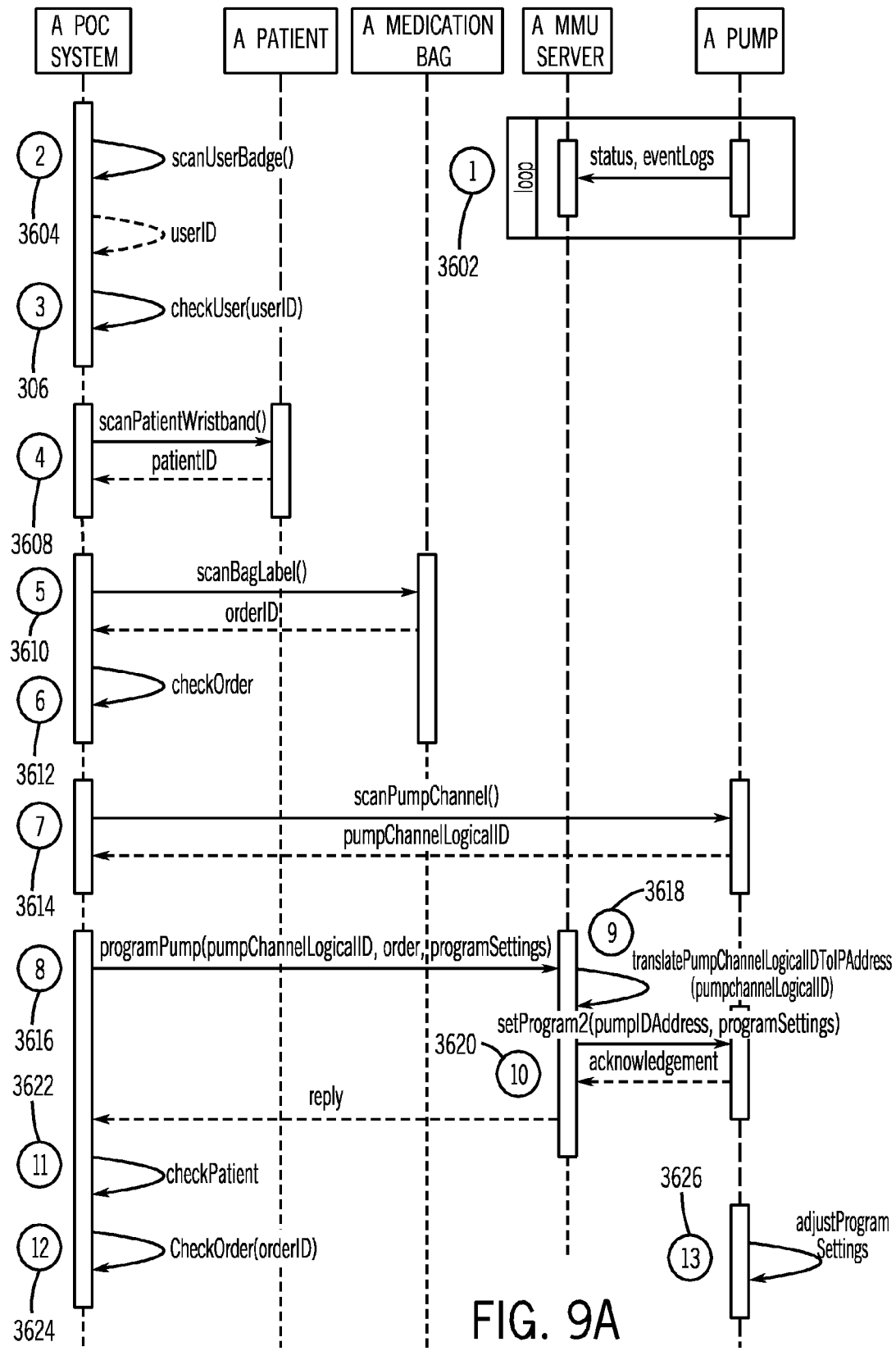
FIG. 9A is a flow chart showing a method for administering a medication to a patient according to one embodiment of the present invention.
Figure 9B:
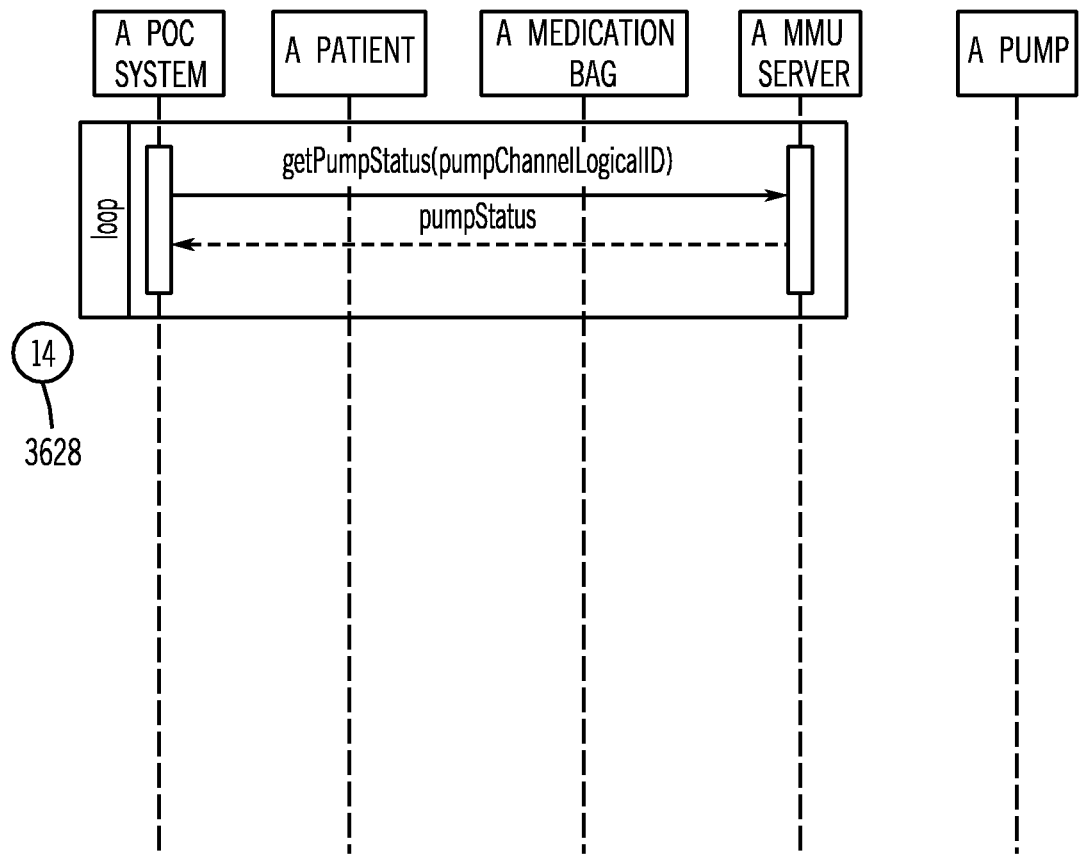
FIG. 9B is a continuation of the flow chart of FIG. 9A.
Figure 10A:
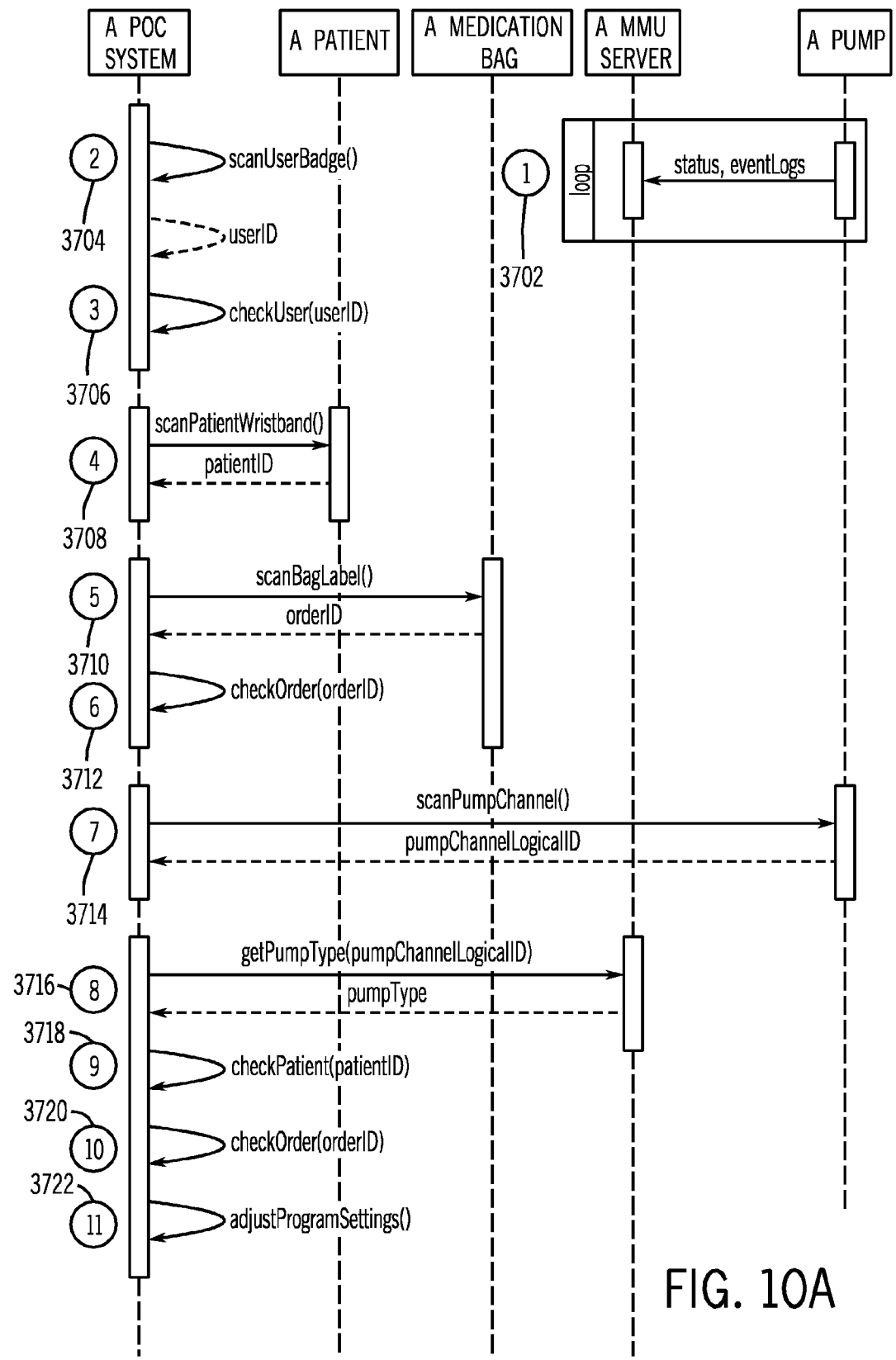
FIG. 10A is a flow chart showing a method for administering a medication to a patient according to one embodiment of the present invention.
Figure 10B:
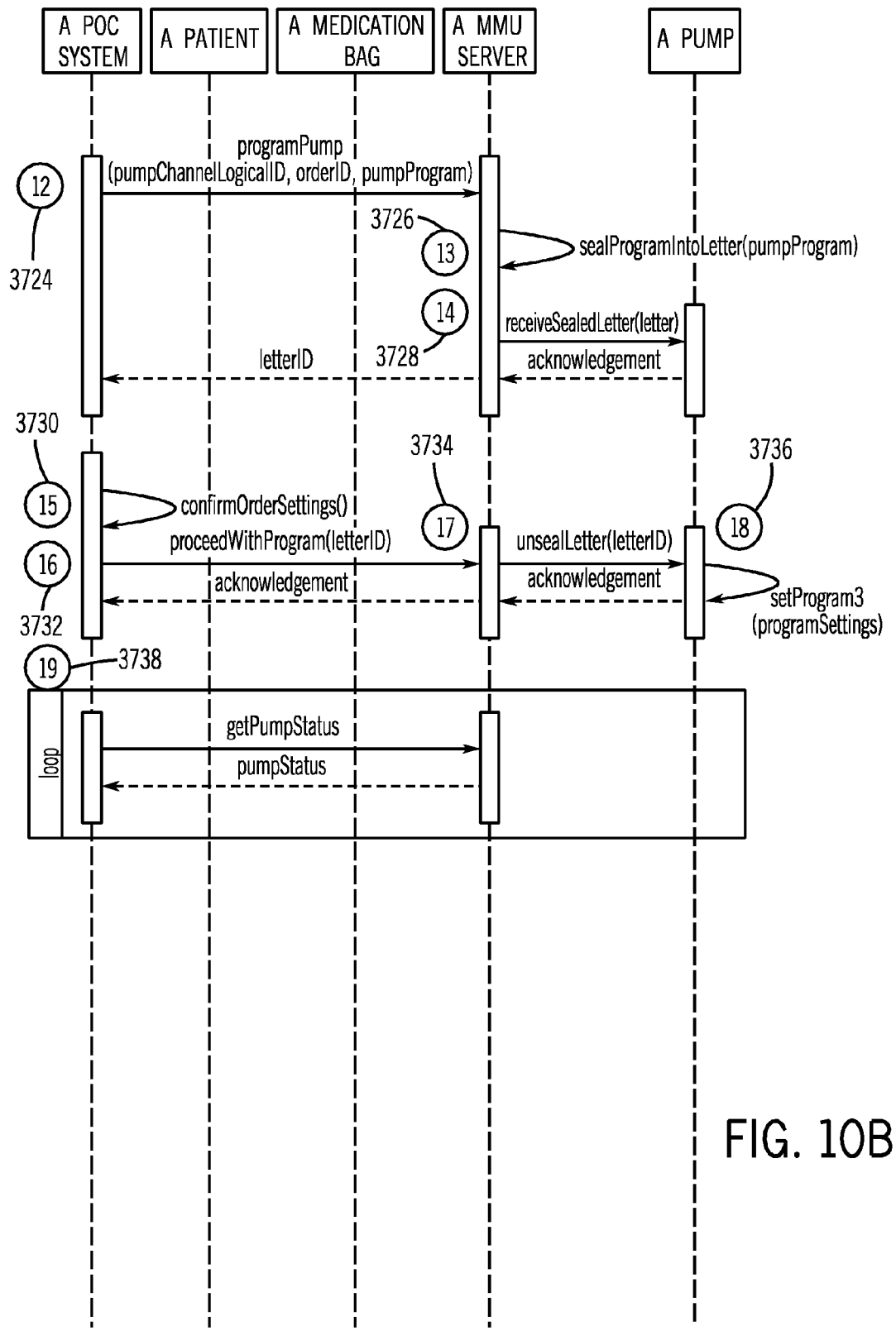
FIG. 10B is a continuation of the flow chart of FIG. 10A.

Referring to flowcharts of FIGS. 9A and 9B in addition to FIGS. 1, 2 and 5, another embodiment of the system and method of administering a medication 3100, 3200 to a patient 3104, 3204 using an infusion pump 3130, 3230 is shown. Specifically, this MMU server mediated embodiment is substantially similar to the previous embodiments where the medical device specific delivery information, including a program, is transmitted to the infusion pump 3130, 3230 from the POC system 3125, 3225 through the MMU computer 3108, 3208 before the patient 3104, 3204 is positively identified. This embodiment is similar to the embodiment of FIGS. 8A and 8B in the first through the twelfth process steps 3602-3624. However, instead of the nurse 3132, 3232 making program adjustments at the POC system 3125, 3225, in a thirteenth process step 3626, adjustments are made by the nurse 3132, 3232 using the user interface 86 and the display 88 of the pump. In an fourteenth process step 3628, the POC system 3125, 3225 may then poll the MMU computer 3108, 3208 for status information about an infusion pump channel using the channel's logical ID. Thus, the POC system learns of any program adjustments made at the pump 3130, 3230. This embodiment advantageously has fewer steps yet allows for program adjustments. Any adjustments made will also be subject to the safety limits of the drug library of the pump and will give the caregiver immediate alarm feedback if the adjusted pump program settings are not within such limits.

With reference to FIGS. 10A and 10B and FIGS. 1 and 2, another server mediated embodiment is shown. This embodiment, which is called a server mediated "unopened letter" programming model, is similar to the previously described server mediated embodiments through the first seven process steps 3702-3714. In a eighth process step 3716, the POC system 3125, 3225 transmits a request to the MMU computer 3108, 3208 for the type of infusion pump 3130, 3230 based upon the given logical ID of the pump/pump channel. At this point, the POC system 3125, 3225 can then utilize the information concerning the type of infusion pump 3130, 3230 to adjust or tailor the workflow, communications, and the user interface itself (on the POC client 3126, 3226 and elsewhere) so as to be appropriate for the type of infusion pump 3130, 3230 being used. In a ninth process step 3718, the POC system 3125, 3225 checks the patient ID or performs a "right patient" check as a part of the "five rights" checking. The right patient check and other checks alternatively can be postponed until just prior to the final confirmation of order settings in step fifteen described below. In a tenth process step 3720, the POC system 3125, 3225 performs any additional "five rights" checking and/or other checking on the order (e.g. right time, allergies, drug-drug interactions, etc.). In an eleventh process step 3722, the nurse 3132, 3232 can adjust and confirm the medical device specific delivery information, such as the program settings through the POC system 3125, 3225, such as through the POC client 3126, 3226.

In a twelfth process step 3724, the POC system 3125, 3225 sends or transmits the medical device specific identification information, such as the pump or pump channel ID, the caregiver specific identification information, such as the nurse's ID, the patient specific identification information, such as the patient ID, the order ID and the medical device specific delivery information, such as the pump settings for the order, to the MMU computer 3108, 3208.

In a thirteenth process step 3726, the MMU 3108, 3208 bundles at least the pump settings for the order and optionally any of the other information received from the POC system 3125, 3225 into a sealed program information letter and assigns it a unique letter ID. In a fourteenth process step 3728, the MMU 3108, 3208 transmits the sealed program information letter and letter ID to the pump 3130, 3230. The pump 3130, 3230 receives the letter and acknowledges to the MMU 3108, 3208 that the letter was received, but cannot open the letter except in response to a unseal letter message from the MMU 3108, 3208. The MMU 3108, 3208 sends the letter ID to the POC system 3125, 3225.

In a fifteenth process step 3730, the nurse 3132, 3232 confirms the order settings at the POC client 3126, 3226. In a sixteenth process step 3732, the nurse 3132, 3232 presses a button on the POC client 3126, 3226 to transmit a signal from the POC system 3125, 3225 to the MMU 3108, 3208 to proceed with the program for the given letter ID. In a seventeenth process step 3734, the MMU 3108, 3208 transmits a command to the pump 3130, 3230 to unseal the program pump information letter associated with the given letter ID. In an eighteenth step 3736, the pump 3130, 3230 unseals the program pump letter, sets the infusion settings in its memory and displays them, then sends an acknowledgement to the MMU 3108, 3208, which in turn transmits an acknowledgement to the POC system 3125, 3225. As in previously described embodiments, the POC system 3125, 3325 polls the MMU 3108, 3208 to get pump status information in a nineteenth step 3738.

Referring to FIGS. 1, 2, 11A and 11B, another embodiment of the system and method of administering a medication 3100, 3200 to a patient 3104, 3204 using an infusion pump 3130, 3230 is shown. In this embodiment, the infusion pump 3130, 3230 pulls its program information from a remote computer within the system in response to a request from the nurse 3132, 3232 at the infusion pump 3130, 3230.

In this embodiment, a first process step 3802 provides that the MMU computer 3108, 3208 continually receives asynchronous (i.e. unsolicited, un-polled) status messages and event logs from the infusion pump 3130, 3230 and stores this information in an associated memory for purposes of at least displaying infusion pump 3130, 3230 status and generating reports. Alternatively, the MMU computer 3108, 3208 can poll the infusion pump 3130, 3230 and synchronously receive information from the infusion pump 3130, 3230.

In a second process step 3804, as in prior embodiments, the nurse 3132, 3232 can optionally start the workflow for auto-programming of the infusion pump 3130, 3230 by using the POC system 3125, 3225 to scan the identifier on the nurse's ID badge 116. In a substep 3805, the POC system 3125, 3225 determines if the nurse 3132, 3232 is a valid authorized user of the POC system 3125, 3225. This enhances patient safety by preventing unauthorized infusions and facilitates electronic documentation of infusion orders administered. The POC system 3125, 3225 may also require the nurse 3132, 3232 to enter a password, and/or other information at the POC system 3125, 3225 or at the infusion pump 3130, 3230.

In a third process step 3806, the nurse 3132, 3232 at the POC system 3125, 3225 scans the identifier on the patient's wristband 112. The resultant patient ID, which may be a medical record number, an account number or some other identifier that the care facility uses to positively identify the patient, is retained in a memory in the POC system 3125, 3225.

In a fourth process step 3808, the nurse 3132, 3232 obtains the container 3102, 3202 of medication 3100, 3200 and scans the identifier 3101, 3201 on the identification label 102 on the container 3102, 3202. The container ID 3101, 3201, which may comprise machine-readable indicia such as a bar code, RFID tag, or the like, can be a universally unique order ID so that the POC system 3125, 3225 can retrieve information about the associated medication order without having to scan the patient ID on the patient wristband 112 or rely on such patient ID information for comparison purposes. Alternatively, the container ID can be a composite ID that includes patient ID or some portion thereof and an order ID related to that particular patient. Alternatively, the container ID can be an absolute or unique pharmacy order identifier that can be generated by the order entry or pharmacy information systems. Alternatively, for commonly used containers that are stocked on the ward or patient care floor, like dextrose, saline or other solutions, the container ID may be a medication ID that includes only medication-specific information, including but not limited to medication name, concentration (if applicable) and volume.

In a fifth process step 3810, the POC system 3125, 3225 determines that the medication is potentially "pump-able" and either transmits a query to the POC client 3126, 3226 asking the nurse 3132, 3232 if the nurse wants to deliver the medication using an infusion pump 3130, 3230. The POC computer 3124, 3224 and/or the POC client 3126, 3226 can accept a yes/no response to the query or the POC system 3125, 3225 can accept a response of the nurse 3132, 3232 actually scanning an identifier 92 for an infusion pump 3130, 3230 or pump channel thereof If the nurse 3132, 3232 scans the identifier 92 of the infusion pump 3130, 3230 channel as the response, the POC system 3125, 3225 receives a pump channel logical ID from the scanned barcode and stores it in memory.

In an optional alternative sixth process step 3812, the POC system 3125, 3225 transmits a request to the MMU computer 3108, 3208 requesting the pump type of infusion pump 3130, 3230 based upon the given logical ID of the pump/pump channel. In response, the MMU computer 3108, 3208 transmits or provides to the POC system 3125, 3225 the pump type corresponding to the logical ID of the scanned infusion pump or pump channel. The POC system 3125, 3225 can then tailor its subsequent workflow to the particular type of pump 3130, 3230. For example, different prompts, checks, screens, and warnings may be provided by the POC system 3125, 3225 for syringe, peristaltic, cassette, general infusion, elastomeric and patient controlled analgesia pumps.

In a seventh process step 3814, the POC system 3125, 3225 checks the patient ID or performs a "right patient" check as a part of the "five rights" checking. The right patient check and other checks alternatively can be postponed until just prior to adjustment or the final confirmation of order settings at the pump 3130, 3230 in step 3830 described below (the program settings will have been received at the pump). The POC system 3125, 3225 can also perform additional checking based on the patient ID, order ID and/or the container ID (e.g. right time, allergies, drug-drug interactions, etc.).

In an optional eighth process step 3816, the nurse 3132, 3232 can adjust and confirm the medical device specific delivery information, such as the program settings through the POC system 3125, 3225, for example through the POC client 3126, 3226. In a ninth process step 3818, the POC system 3125, 3225 submits pump program information including a generically formatted (non-pump specific) pump program and the pump channel logical ID to the MMU server 3108, 3208. It is important to note that the generic pump program is incapable of operating the pump.

In a tenth process step 3820, the MMU server 3108, 3208 gets from its memory the pump type corresponding to the logical ID of the scanned infusion pump or pump channel, if step 3812 was previously omitted. Of course, if step 3812 was previously executed, the pump type information could be included in the pump program information provided to the MMU 3108, 3208 by the POC system 3125, 3225 instead of or in addition to the pump channel logical ID. The MMU 3108, 3208 uses the pump type information and the generic pump program to generate a specific pump program that is acceptable to the particular type of pump. In other words, the MMU 3108, 3208 translates the generic program into one specific to the particular type of pump 3130, 3230. The MMU 3108, 3208 converts the logical ID of the scanned pump 3130, 3230 to a pump IP address by consulting a dynamic IP address lookup table in the memory of the MMU 3108, 3208. The MMU 3108, 3208 does not download the program to the pump 3130, 3230 in response to the above steps. Instead, the MMU 3108, 3208 holds onto the pump program and acts like a post office holding a letter addressed to the pump 3130, 3230.

The MMU 3108, 3208 can also perform additional functions of establishing and monitoring time stamps on pump programs, as well as managing multiple infusion programs destined for the same pump 3130, 3230. Programs can be made available to the same pump 3130, 3230 on a first-in-first-out (FIFO) basis, last-in-first-out (LIFO) or other priority basis. For example, boluses might be prioritized for delivery before maintenance doses and "crash cart" or "code blue" response drugs might be given top priority. LIFO can be used to insure that only the most recent or most recently modified order is available to the pump 3130, 3230. The MMU 3108, 3208 can automatically expire unutilized pump programs or send alarms or error messages to the pump 3130, 3230 and/or POC system 3125, 3225 when a time stamp from the MMU or POC system indicates a program age greater than a predetermined program age. Thus, stale, superseded, or out-of-date orders can be removed from the queue.

In an eleventh process step 3822, the MMU 3108, 3208 sends a message to the pump 3130, 3230 stating that a pump program is available for the pump to pull. Returning to the post office analogy, the MMU 3108, 3208 tells the pump 3130, 3230, "You have mail." The pump 3130, 3230 displays a message on its display 88 that tells the nurse 3132, 3232 to load the program when ready. The MMU 3108, 3208 sends a message to POC system 3125, 3225 indicating that it successfully received the generic pump program, translated the generic pump program into a pump-specific program, and advised the pump 3130, 3230 of the availability of the specific pump program. The last-mentioned message from the MMU 3108, 3208 signals the conclusion of the programming-related transactions between the MMU 3108, 3208 and the POC system 3125, 3225. In an optional twelfth process step 3824, receipt of the message from the MMU 3108, 3208 triggers the POC system 3125, 3225 to display a prompt on the POC client 3126, 3226 instructing the nurse 3132, 3232 to go to the pump 3130, 3230 to load the program on the pump 3130, 3230. This is especially useful if the nurse 3132, 3232 is not presently looking at the pump display 88 or proximate to it.

In a thirteenth process step 3826, the nurse 3132, 3232 uses the keypad 86 or display 88 to instruct the pump 3130, 3230 to retrieve or pull the pump specific program from the MMU 3108, 3208. In a fourteenth process step, the pump 3130, 3230 retrieves or pull the pump specific program from the MMU 3108, 3208. In a fifteenth process step 3830, the nurse 3132, 3232 can adjust (modify) the program settings on the pump 3130, 3230, if desired. Then, as illustrated in FIG. 4, the nurse 3132, 3232 must confirm or cancel the settings by pressing an appropriate button on the keypad 86 or touching a designated area of the display 88 when the display is a touch screen. Upon confirmation, the pump 3130, 3230 prompts the nurse 3132, 3232 with a second screen asking if they are ready to start the infusion. Upon receipt of an affirmative response from the nurse 3132, 3232, the pump 3130, 3230 runs the programmed infusion.

In a sixteenth process step 3832, the POC system 3125, 3225 periodically requests pump status information from the MMU 3108, 3208. The pump status supplied by the MMU 3108, 3208 will either provide a positive confirmation that the program is running on the pump 3130, 3230 or a negative indication that the program has been rejected. Based upon the pump status or after a predetermined period of time has elapsed or by direct intervention by the nurse 3132, 3232, the POC system 3125, 3225 removes its prompt to load the program on the pump, if step 3824 was executed. Alternatively, pump status messages can be supplied when the pump 3130, 3230 is on but not in an active pumping state, such as when the program settings have been received or when the program settings have been confirmed but the pump 3130, 3230 has not been started by the nurse 3132, 3232.

Figure 11A:
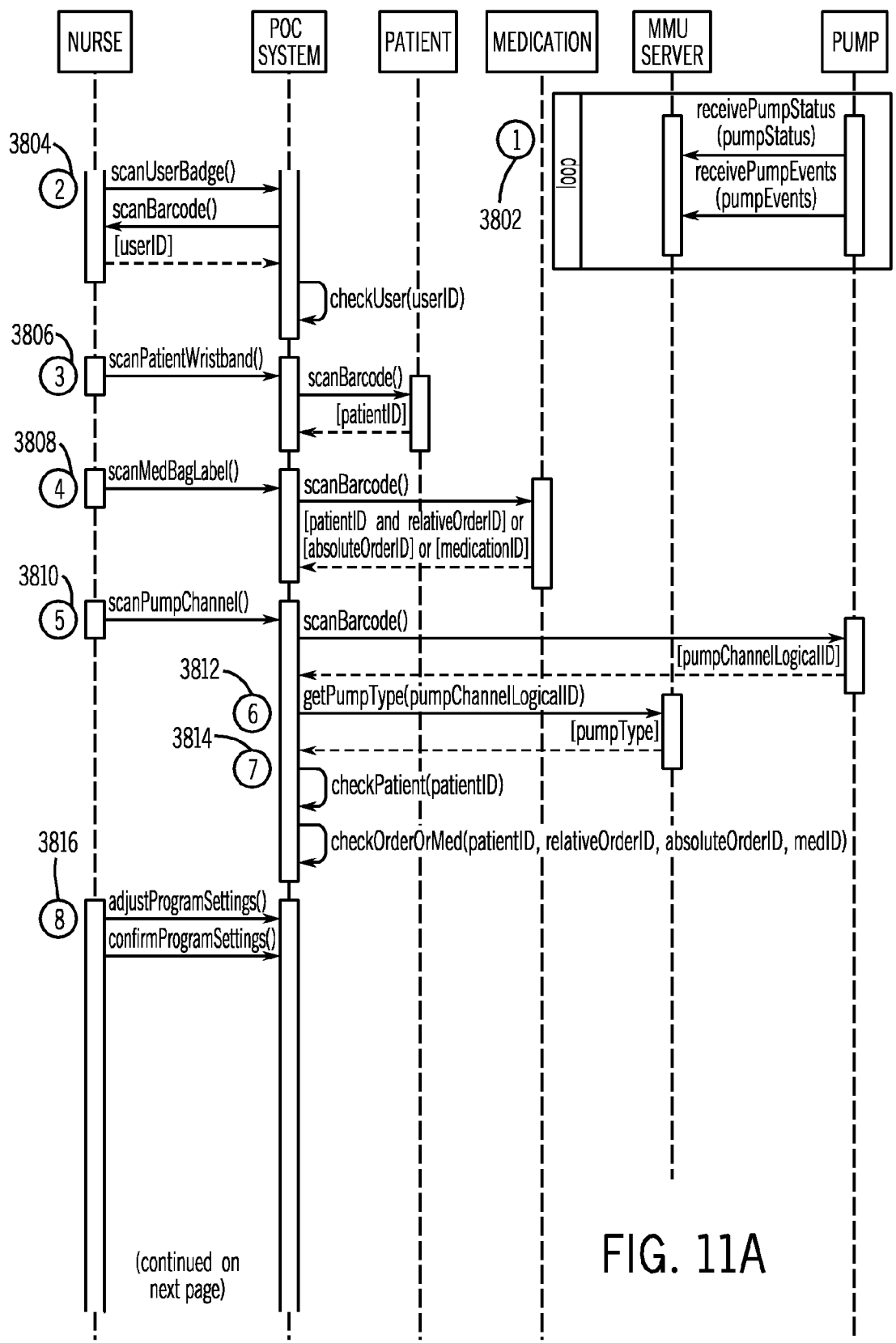
FIG. 11A is a flow chart showing a method for administering a medication to a patient according to another embodiment of the present invention.
Figure 11B:
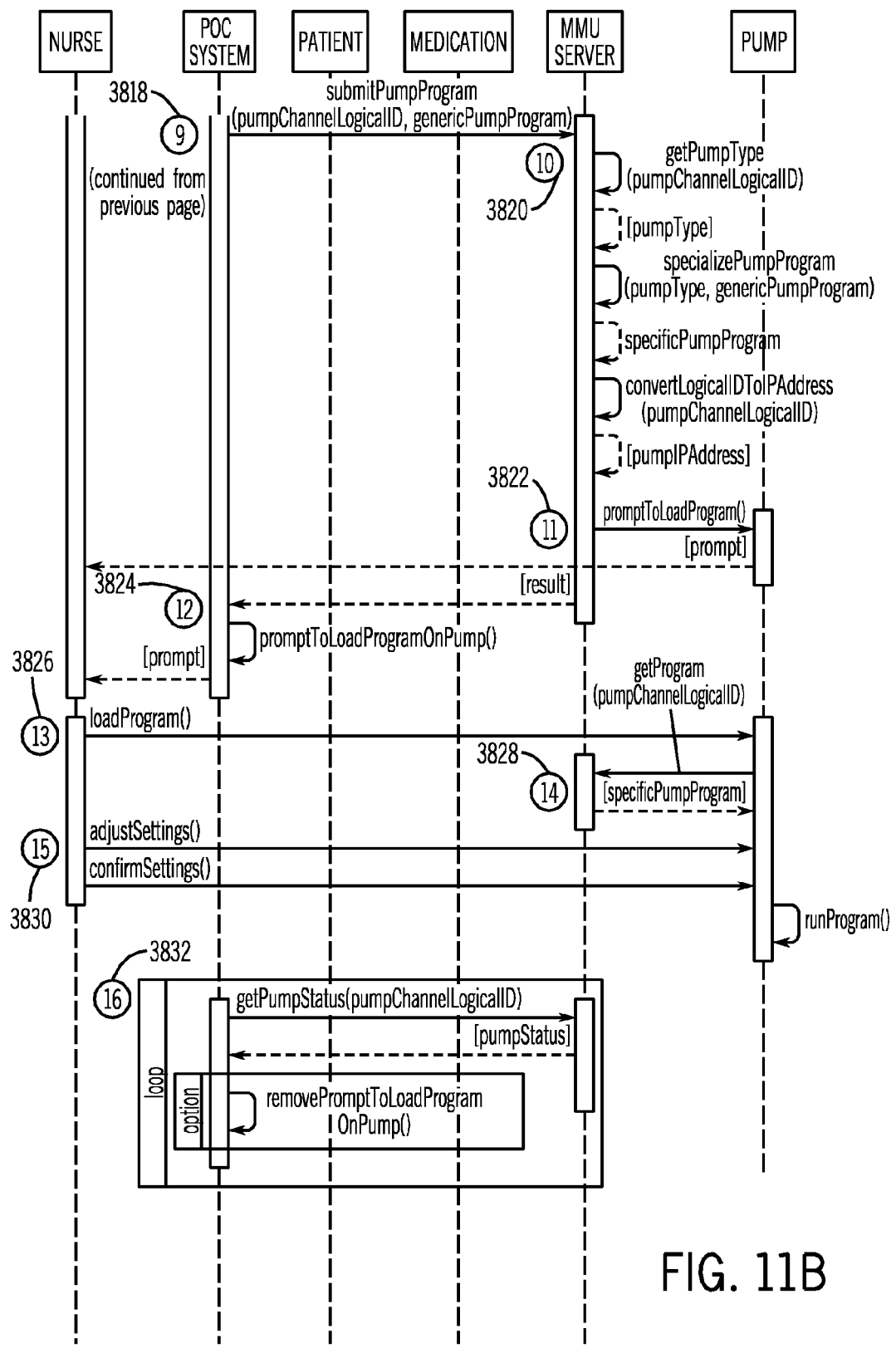
FIG. 11B is a continuation of the flow chart of FIG. 11A.

The embodiment of FIGS. 11A and 11B is advantageous in that it is flexible enough to fit with the workflows of most clinical POC systems. This embodiment decouples the three major processors in the system (the pump, the MMU and the POC system), which allows for more efficient asynchronous communication, scales well if many pumps need to be communicated with, and provides greater security by preventing the POC system 3125, 3225 from programming the pump 3130, 3230 directly without permission from the MMU 3108, 3208. This embodiment is also flexible enough to allow additional checks to be done by the MMU 3108, 3208, if desired. Advantageously program settings can be ready, waiting and perhaps even scheduled for a particular pump 3130, 3230 before the pump is available.

Figure 12:
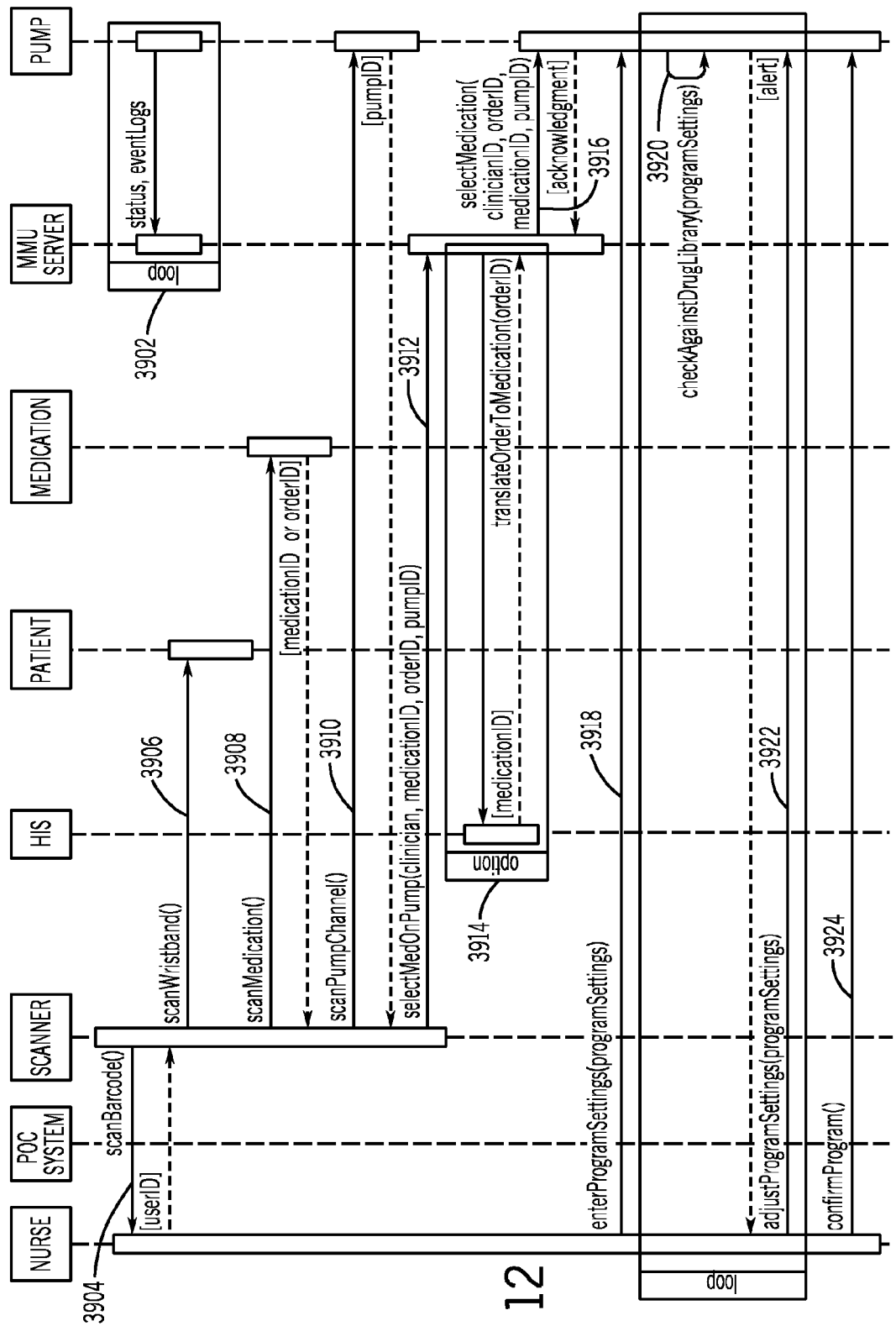
FIG. 12 is a flow chart showing a method for administering a medication to a patient according to another embodiment of the present invention.

Referring to FIGS. 1, 2 and 12, another embodiment of the system and method of administering a medication 3100, 3200 to a patient 3104, 3204 using an infusion pump 3130, 3230 is shown. This embodiment is called the "medication selection" workflow and works with a stand alone scanner or one associated with a POC system 3125, 3225, MMU 3108, 3208, or a pump 3130, 3230. In this embodiment, a first process step 3902 provides that the MMU computer 3108, 3208 continually receives asynchronous (i.e. unsolicited, un-polled) status messages and event logs from the infusion pump 3130, 3230 and stores this information in an associated memory for purposes of at least displaying infusion pump 3130, 3230 status and generating reports. Alternatively, the MMU computer 3108, 3208 can poll the infusion pump 3130, 3230 and synchronously receive information from the infusion pump 3130, 3230.

In a second process step 3904, similar to the previously described embodiments, the nurse 3132, 3232 can optionally start the workflow for auto-programming of the infusion pump 3130, 3230 by using the scanner to scan the identifier on the nurse's ID badge 116. The scanner is in communication with the MMU server 3108, 3208 via a wireless connection, although a wired connection is also possible. The scanner can be disposed on or in the pump 3130, 3230, tethered or wired thereto, or in wireless communication therewith directly or through the MMU 3108, 3208.

In a third process step 3906, the nurse 3132, 3232 uses the scanner to scan the identifier on the patient's wristband 112. The patient ID, which may be a medical record number, an account number or some other identifier that the care facility uses to positively identify the patient, is retained in a memory in the scanner.

In a fourth process step 3908, the nurse 3132, 3232 obtains the container 3102, 3202 of medication 3100, 3200 and uses the scanner to scan the identifier 3101, 3201 on the identification label 102 on the container 3102, 3202. The container ID 3101, 3201, which may comprise machine-readable indicia such as a bar code, RFID tag, or the like, can be a universally unique order ID so that the HIS 3110, 3210 or POC system 3125, 3225 can retrieve information about the associated medication order without having to scan the patient ID on the patient wristband 112 or rely on such patient ID information for comparison purposes. Alternatively, the container ID can be a composite ID that includes patient ID or some portion thereof and an order ID related to that particular patient. Alternatively, the container ID can be an absolute or unique pharmacy order identifier that can be generated by the order entry or pharmacy information systems. Alternatively, the container ID may be a medication ID that includes only medication-specific information, including but not limited to medication name, concentration (if applicable) and volume. For this example, the medication ID includes a generic, brand or package level identification of the medication and its concentration as well. The container ID can include the order ID or the medication ID or both.

In a fifth process step 3910, if the nurse wants to deliver the medication using an infusion pump 3130, 3230, the nurse 3132, 3232 scans the identifier 92 of the infusion pump 3130, 3230 channel and the scanner receives a pump channel logical ID or pump ID from the scanned barcode and stores it in memory.

In a sixth process step 3912, the scanner sends a select medication on pump message to the pump 3130, 3230. The message may be routed indirectly through the MMU server 3108, 3208 or sent directly to the pump 3130, 3230. The message preferably includes the medication ID and may include additional scanned information including the order ID, pump or channel ID, and clinician ID. If the message was sent to the MMU 3108, 3208 and only an order ID was provided, the MMU can assist in an optional seventh process step 3914 wherein the medication (and concentration) contained in the order are determined by requesting this information or translation from the pharmacy information system 3116, 3216 or order entry system 3114, 3214 of the HIS 3110, 3210 or accessing information already cached on the MMU 3108, 3208 by virtue of a separate MMU/HIS interface. Of course, this supplemental information or translation can be provided to the pump 3130, 3230 before, during or after the rest of the selected medication information is sent to the pump, if it is needed. In an eighth process step 3916, the pump 3130, 3230 receives the "select medication" message information and sends an acknowledgement to the MMU 3108, 3208. Once the medication and its concentration are known by the pump 3130, 3230, the pump 3130, 3230 can use this information to automatically populate or fill in certain fields of programming screens, like medication and concentration, and set or identify appropriate drug library rule sets based on the selected CCA. This provides considerable time-savings and adds a layer of safety with the drug library rule sets.

In a ninth process step 3918, the nurse 3118, 3218 enters into the pump 3130, 3230 the remaining pump program settings that have not been automatically populated. Advantageously in a tenth process step 3920, the pump 3130, 3230 checks the entered program settings against the permissible settings specified in the drug library of the pump 3130, 3230 and alerts the nurse of any impermissible settings. The nurse 3132, 3232 can then adjust the pump program settings in an optional step 3922 or override the alert in the case of soft limit violations. Any adjusted pump program settings are also checked against the drug library, and eventually the final program settings are viewed on the pump display screen 88 and confirmed by the nurse 3132, 3232 in process step 3924. Then the nurse 3132, 3232 is presented with a start button on the screen 88 to start the infusion in accordance with the final confirmed programmed pump settings. The pump 3130, 3230 continuously sends status information (i.e., current settings and state) and event logs (i.e., historical activity, alarms, alerts, overrides, etc.) to the MMU 3108, 3208 pursuant to step 3902.

The embodiment of FIG. 12 is advantageous in that it saves the clinician time by automatically populating medication data on the pump, and in so doing enhances the safety of drug administration by invoking or allowing the nurse to quickly select drug library limits already provided on the pump. Many hospitals are non-profit institutions and cannot afford expensive POC systems. However, scanners are far more affordable, ubiquitous and adaptable. The software requirements for this embodiment are more straightforward than many of the other more complex embodiments previously described. The medication is identified only once by all the systems, which saves time and insures that all systems refer to the same medication. This approach is also flexible enough to accommodate medication which are bar coded with order ID or medication ID. The latter case would occur for emergency, "stat", ad hoc, verbal orders, or other situations where the pharmacy information system has not had sufficient time to process the order and label the medication with an order ID barcode. Finally, this approach makes virtually no demands on the POC system, making it easy for hospitals to implement or add on to existing systems and workflows.

Figure 13:
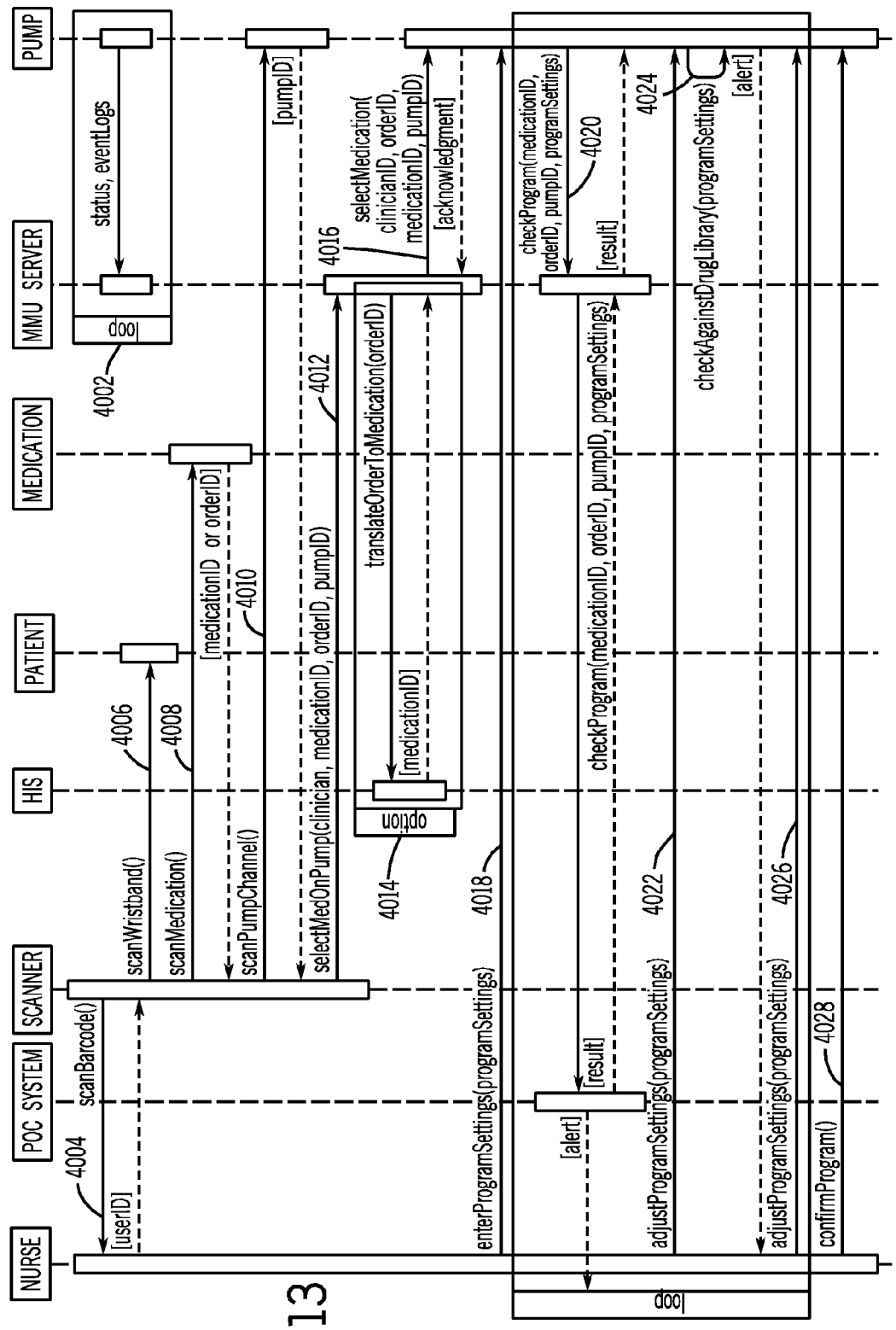
FIG. 13 is a flow chart showing a method for administering a medication to a patient according to another embodiment of the present invention.

Referring to flowchart of FIG. 13 in addition to FIGS. 1 and 2, another embodiment of the system and method of administering a medication 3100, 3200 to a patient 3104, 3204 using an infusion pump 3130, 3230 is shown. This embodiment is called the "medication selection with POC checking" workflow and includes steps 4002, 4004, 4006, 4008, 4010, 4012, 4014 (optional), 4016 and 4018, which are the same as steps 3902, 3904, 3906, 3908, 3910, 3912, 3914, 3916 and 3918 described above relative to FIG. 12. In a tenth process step 4020, the pump 3130, 3230 automatically or upon direction of the nurse 3132, 3232 seeks to check the program information it has been provided. The medication ID, order ID, pump ID and program settings are communicated to the MMU 3108, 3208 by the pump 3130, 3230. The MMU 3108, 3208 in turn communicates the check program message to the POC system 3125, 3225. The POC system 3125, 3225 checks the program information for right patient, right drug, right time, right route, right dose, and other concerns such as right caregiver, allergies, drug-drug interactions, etc. as desired. Results are returned to the MMU 3108, 3208 and the pump 3130, 3230 where they can be reported to the user or displayed to the nurse 3132, 3232. The POC system 3125, 3225 can also provide an alert directly to the nurse.

In an eleventh process step 4022, the nurse 3132, 3232 adjusts program settings (for example, dose, rate, VTBI, duration, etc.) on the pump 3130, 3230 to correct or override the alert condition. In a twelfth process step 4024, the pump 3130, 3230 checks the entered program settings against the permissible settings specified in the drug library of the pump 3130, 3230 and alerts the nurse of any impermissible settings. The nurse 3132, 3232 can then adjust the pump program settings in an optional step 4026 or override the alert in the case of soft limit violations. Any adjusted pump program settings are also rechecked against the POC system requirements and the pump drug library in a repetitive loop, and eventually the final program settings are viewed on the pump display screen 88 and confirmed by the nurse 3132, 3232 in process step 4028. Then the nurse 3132, 3232 is presented with a start button on the screen 88 to start the infusion in accordance with the final check and confirmed programmed pump settings. The pump 3130, 3230 continuously sends status information (i.e., current settings and state) and event logs (i.e., historical activity, alarms, alerts, overrides, etc.) to the MMU 3108, 3208 pursuant to step 4002.

The embodiment of FIG. 13 has all the advantages of the basic medication selection approach of FIG. 12, plus adds POC-based order and medication, as well as POC based checking of the actual infusion parameters programmed into the pump very close in time to the final confirmation and start of delivery.

Figure 14:
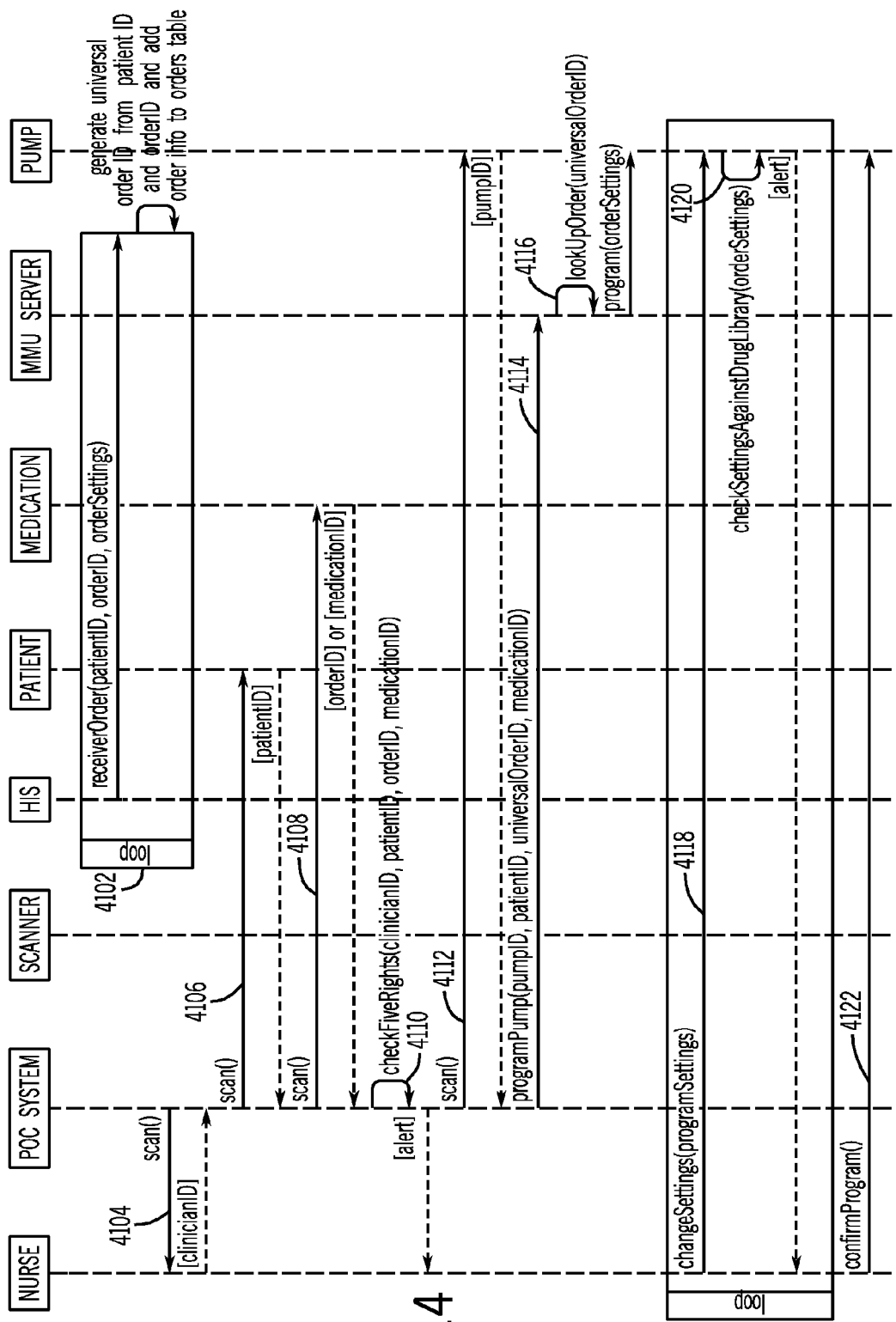
FIG. 14 is a flow chart showing a method for administering a medication to a patient according to another embodiment of the present invention.

FIGS. 1, 2, and 14 illustrate another embodiment of the present invention, which is called the "order lookup" workflow. In a step 4102 of this embodiment, the MMU 3108, 3208 receives a "receive order" message from the HIS 3110, 3210 that includes the patient ID, the order ID, and order settings. Such messages could be received on a synchronous (i.e., polled) or asynchronous (i.e., event driven) basis directly from the HIS or indirectly via an interface engine (not shown). The order ID may be universally unique across all patients or it may be unique only with respect to a given patient. In the latter case, the MMU 3108, 3208 generates a universally unique or universal order ID from the patient ID and the order ID, then forms an orders table wherein the order information is stored according to its universal order ID. For example, the patient ID can be a unique number assigned to the patient by the hospitals admission-discharge-and-transfer system 3112, 3212 and the order ID can be a sequential number representing each medication order written for that particular patient. The sequential number may include the date and time the order is written, the date and time the order is to be administered, or both. The MMU 3108, 3208 generates an absolutely unique or universal order ID and stores the order settings in a lookup table at a cell or location associated with the assigned universal order ID.

The scanner in this embodiment can be associated with the POC system 3125, 3225 as a POC client 3126, 3226. In a second process step 4104, the nurse 3132, 3232 scans his or her caregiver identification badge 116 to input the clinician ID. In a third process step 4106, the nurse 3132, 3232 scans the patient identification bracelet or badge 112 associated with the patient 3104, 3204 to input the patient ID. In a fourth process step 4108, the nurse 3132, 3232 scans the label 102 on the medication container 3100 to obtain either a medication ID or order ID. The second through fourth steps can be performed in any order that is convenient for the caregiver 3132, 3232.

In a fifth process step 4110, the POC system 3125, 3225 checks those "rights" of medication management that it has sufficient information for, such as right/authorized clinician, right patient, right medication, right dose, right route/site, allergies, drug-drug interactions, etc. If anything is not right, the POC system 3125, 3225 generates an alert to the nurse 3132, 3232, typically through the POC client 3126, 3226 and gives the nurse an opportunity to correct the problem or override the alert. Of course, as discussed above, some of the scanning and rights checking can be delayed until after the pump program settings have been sent to the pump 3130, 3230. The POC system 3125, 3225 determines that the medication should be delivered by an IV pump 3130, 3230. In a sixth process step 4112, the nurse 3132, 3232 scans the pump/pump channel bar code label or ID 92 on the pump 3130, 3230.

In a seventh process step 4114, the POC system 3125, 3225 sends a message to the MMU 3108, 3208 telling it to program the pump 3130, 3230. This message must include the pump ID for the pump 3130, 3230 to be programmed and either the patient ID plus order ID, or the universal order ID, and optionally includes the medication ID (including medication name and concentration). The universal order ID or the patient ID plus order ID information allows the MMU 3108, 3208 to look up the order information it previously stored in its orders table and download the order settings to the pump 3130, 3230 in an eighth process step 4116. Because the medication ID also was included with the information sent to the MMU 3108, 3208 by the POC system 3125, 3225, such information can be included with the order settings downloaded to the pump 3130, 3230.

In an optional ninth process step 4118, the nurse can adjust or change the program settings on the pump display 88 or user interface, if desired. Because the medication ID was included with the information sent to the pump 3130, 3230 by MMU 3108, 3208, the pump 3130, 3230 can check the pump settings (whether original, adjusted or changed) in a tenth process step 4120 and provide an alert to the nurse 3132, 3232 on the pump display 88 or as part of pump status at other displays within the hospital. The nurse is prompted to change the program settings on the pump 3130, 3230 or, if permissible, override the alert. The steps 4118 and 4120 continue in a repetitive loop manner until the pump settings meet all the drug library constraints or the associated alerts have been overridden. In an eleventh process step 4122, the nurse 3132, 3232 reviews the final pump settings on the pump display 88 and confirms them with an appropriate affirmative action, response or acknowledgement on the user interface of the pump 3130, 3230. Upon confirmation, the pump 3130, 3230 prompts the nurse 3132, 3232 with a second screen asking if they are ready to start the infusion. Upon receipt of an affirmative response from the nurse 3132, 3232, the pump 3130, 3230 runs the programmed infusion.

As with the other embodiments discussed above, the MMU computer 3108, 3208 can continually receive asynchronous (i.e. unsolicited, un-polled) status messages and event logs from the infusion pump 3130, 3230 and store this information in an associated memory for purposes of at least displaying infusion pump 3130, 3230 status and generating reports. This step has been omitted from FIG. 14 for the sake of brevity. It will also be understood by one of ordinary skill in the art based upon the present description that the MMU can poll the pump 3130, 3230 and receive synchronous communication regarding status and event logs.

Figure 15:
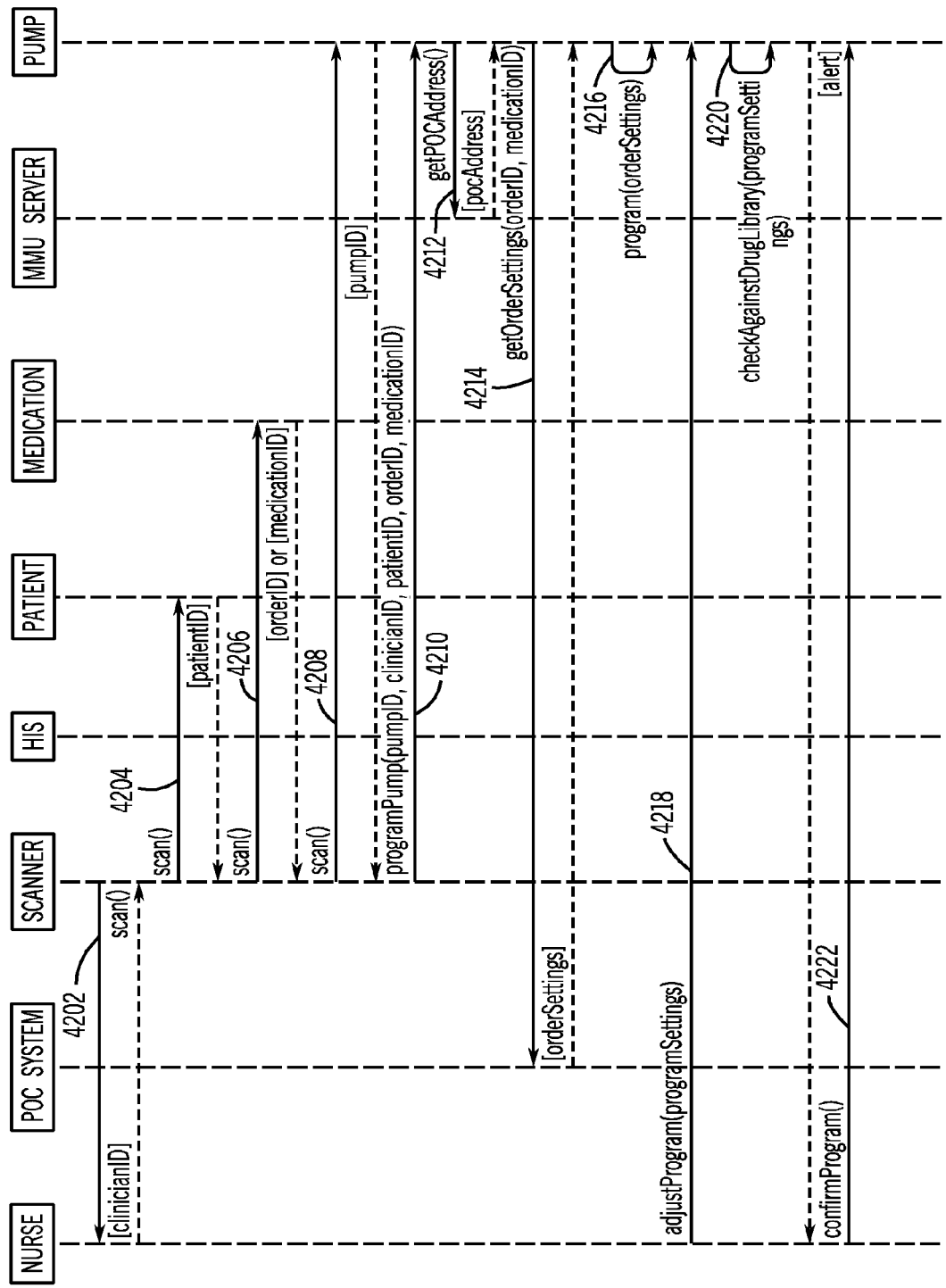
FIG. 15 is a flow chart showing a method for administering a medication to a patient according to another embodiment of the present invention.

FIGS. 1, 2 and 15 illustrate another embodiment of the present invention. This embodiment is called a "pump-centric order settings acquisition" workflow. Like the embodiments of FIGS. 12 and 13, a scanner for machine readable indicia is provided. The scanner can be associated with the pump 3130, 3230, the MMU 3108, 3208, or the POC system 3125, 3225. The scanner can be a stand alone device communicating in a wired or wireless manner with the pump 3130, 3230, with the POC system 3125, 3225 as a POC client 3126, 3226, or even with the MMU 3108, 3208 as a client. The scanner can be mounted on or in the pump 3130, 3230.

In a first process step 4202, the nurse 3132, 3232 scans his or her caregiver identification badge 116 to capture the clinician ID. In a second process step 4204, the nurse 3132, 3232 scans the patient identification bracelet or badge 112 associated with the patient 3104, 3204 to capture the patient ID. In a third process step 4206, the nurse 3132, 3232 scans the label 102 on the medication container 3100 to capture either a medication ID or order ID. In a fourth process step 4208, the nurse 3132, 3232 scans the pump or pump channel label or ID 92 on the pump 3130, 3230 to capture the pump ID. The first through fourth steps can be performed in any order that is convenient for the caregiver 3132, 3232. In a fifth process step 4210, a program pump message is sent from the scanner to the pump 3130, 3230. The message can be sent directly to the pump 3130, 3230 from the scanner or it can be sent through the MMU 3108, 3208. The message can include the pump ID, clinician ID, patient ID and either the order ID or the medication ID.

In a sixth process step 4212, the pump 3130, 3230 queries the MMU 3108, 3208 for the IP address of the POC system 3125, 3225. The MMU 3108, 3208 provides the pump 3130, 3230 with the IP address of the POC system 3125, 3225. In a seventh process step 4214, the pump 3130, 3230 sends a "getOrderSettings" message to the POC system 3125. The message includes the order ID or the medication ID and can include further information such as the patient ID. The POC system 3125, 3225 responds by providing or sending the order settings to the pump. This communication preferably occurs directly, but can take place indirectly through the MMU 3108, 3208 without detracting from the invention. In an eighth process step 4216, the pump 3130, 3230 automatically populates the program setting fields on the pump with the order settings it received from the POC system 3125, 3225 or the scanner earlier and any other values that can be calculated from those settings.

In an optional ninth process step 4218, the nurse 3132, 3232 can adjust the program settings on the pump 3130, 3230, typically on the user interface and display 88 of the pump. In a tenth process step 4220, the pump checks the program settings against the limits of its drug library, thanks to the medication ID it received from the scanner. Ideally, the medication ID includes medication-specific information, including but not limited to medication name, concentration (if applicable) and perhaps volume. For this example, the medication ID includes a generic, brand or package level identification of the medication and its concentration as well. If the user customizable drug library limits are violated by the original or adjusted program settings, the pump 3130, 3230 generates an alert on its display 88 or other displays within the hospital. The adjust settings, check settings against drug library, and alert steps may be performed repeatedly in a loop until the nurse has corrected or overridden any alerts. In an eleventh process step 4222, the nurse reviews and confirms the program on the pump 3130, 3230 as described previously and is presented with another screen to actually start the programmed infusion.

As with the other embodiments discussed above, the MMU computer 3108, 3208 can continually receive asynchronous (i.e. unsolicited, un-polled) status messages and event logs from the infusion pump 3130, 3230 and store this information in an associated memory for purposes of at least displaying infusion pump 3130, 3230 status and generating reports. This step has been omitted from FIG. 15 for the sake of brevity. It will also be understood by one of ordinary skill in the art based upon the present description that the MMU can poll the pump 3130, 3230 and receive synchronous communication regarding status and event logs.

Any process descriptions or blocks in the figures may be understood as representing modules, segments, or portions of code which include one or more executable instructions for implementing specific logical functions or steps in the process, and alternate implementations are included within the scope of the embodiments of the present invention in which functions may be executed out of order from that shown or discussed, including substantially concurrently or in reverse order, depending on the functionality involved, as would be understood by those having ordinary skill in the art. One skilled in the art will appreciate the order of the many of the steps in the above embodiments can be changed, as necessary to conform to hospital practices and desired workflow.

One skilled in the art will also appreciate that the present invention could be applied to a remote clinic or ambulatory home care environment and that the patient may serve as his or her own caregiver such that scanning the patient may determine both the authorized user or clinician ID and the patient ID.

It will be understood that the invention may be embodied in other specific forms without departing from the central characteristics thereof. The present embodiments, therefore, are to be considered in all respects illustrative and not restrictive, and the invention is not to be limited to the details given herein.

What is claimed is:

1. A method for programming a medical device, comprising the steps of:
    capturing with an input means at least a medical device identifier associated with the medical device and additional identification information including a medication container identifier associated with a container containing a medication, the medication container identifier including at least one of an order ID and a medication ID;
    transmitting a message to a medication management computer in communication with the medical device and a hospital information system, the message including at least the medical device identifier and the additional identification information;
    providing from the hospital information system to the medication management computer at least one component of the medication container identifier that corresponds to the previously received order ID or medication ID, wherein the at least one component is different from the order ID, medication ID, or message previously received by the medication management computer;
    providing from the hospital information system to the medication management computer a medication name and a concentration that correspond to the medication ID;
    transmitting from the medication management computer to the medical device a select medication message that includes the medication name and the concentration and allows the medical device to automatically select a drug library rule set from a drug library resident in a memory of the medical device;
    manually entering program settings at the medical device;
    comparing the program settings to the drug library rule set;

if there are any violations of the drug library rule set, generating an alert;

undertaking one of the steps of entering adjusted program settings and overriding the alert;

repeating the comparing, generating, adjusting and overriding steps until all violations of the drug library rule set have been resolved; and confirming the program settings at the medical device.

2. The method of claim 1, wherein the additional identification information includes a clinician ID and the select medication message includes the clinician ID, order ID, medication ID and medical device identifier.

3. A system for programming a medical device having a drug library including drug library rule sets, comprising;

an input means for capturing at least a medical device identifier associated with the medical device and additional identification information including a medication container identifier associated with a container containing a medication, the medication container identifier including at least one of an order ID and a medication ID;

a hospital information system computer;

a medication management computer in communication with the medical device and the hospital information system computer;

wherein the input means transmits a message including at least the medical device identifier and the additional identification information to the medication management computer;

wherein the medication management computer acquires from the hospital information system at least one component of the medication container identifier that corresponds to the previously received order ID or medication ID, wherein the at least one component is different from the order ID, medication ID, or message previously received by the medication management computer;

wherein the medication management computer acquires a medication name and a concentration that correspond the medication ID from the hospital information system and transmits a select medication message that includes the medication name and the concentration to the medical device;

wherein the medical device automatically selects a drug library rule set from the drug library based upon the medication name and the concentration included in the select medication message;

wherein the medical device receives manually entered program settings, compares the manually entered program settings to the selected drug library rule set, and generates an alert if a violation occurs;

wherein a user of the medical device can take one of the following actions to resolve the alert before confirmation the program settings:

1) adjust the program settings on the medical device; and
2) override the alert.

4. The system of claim 3, wherein the additional identification information includes a clinician ID and the select medication message includes the clinician ID, the order ID, the medication ID and the medical device identifier.

5. The system of claim 4, wherein the additional identification information includes patient identification information and the system further comprises a POC system computer in communication with the medication management computer for comparing any of the additional identification information to identification information stored in a memory associated with the POC system computer and generating an alert if there is a mismatch.

6. The system of claim 5, wherein the medical device reports the program settings to the POC system computer after manual entry and the POC system computer compares the program settings to medication safety guidelines stored in the memory of the POC computer.

7. The system of claim 6, wherein the medical device reports the program settings to the POC system computer via the medication management computer.

* * * * *